United States Patent [19]

Wentworth et al.

[11] 4,235,799
[45] Nov. 25, 1980

[54] PRODUCTION OF METHANOL

[76] Inventors: Theodore O. Wentworth; Alvin B. Stiles, both c/o Wentworth Brothers Incorporated, 644 Linn St., Cincinnati, Ohio 45203

[21] Appl. No.: 30,028

[22] Filed: Apr. 16, 1979

[51] Int. Cl.$^2$ ............................................. C07C 31/06
[52] U.S. Cl. .................................................. 260/449.5
[58] Field of Search .............. 260/449.5, 449 R, 449 S

[56] References Cited

U.S. PATENT DOCUMENTS

| | | | |
|---|---|---|---|
| 1,820,417 | 8/1931 | Williams | 260/449.5 |
| 1,921,776 | 8/1933 | Richardson | 260/449.5 |
| 2,904,575 | 9/1959 | Peet | 260/449.5 |

FOREIGN PATENT DOCUMENTS 1259945 1/1972 United Kingdom .................. 260/449.5

OTHER PUBLICATIONS

Mehta, Hydrocarbon Processing, May 1976, pp. 165–168.

Primary Examiner—Howard T. Mars
Attorney, Agent, or Firm—Thomas E. Spath

[57] ABSTRACT

Methanol is produced by passing a mixture of hydrogen and one or more carbon oxides into contact with at least two beds (converters) of catalyst arranged in series, the beds of catalyst being operated at increasing temperature levels in the direction of flow of the mixture. The mixture is then cooled by indirect heat-exchange and passed into contact with at least one further bed of catalyst.

14 Claims, 7 Drawing Figures

PRODUCTION OF METHANOL

SUMMARY OF THE INVENTION

When synthetic methanol is produced by passing a mixture of hydrogen and one or more carbon oxides (carbon monoxide, carbon dioxide, or a mixture of carbon monoxide and carbon dioxide) into contact with a catalyst under elevated conditions of temperature and pressure, the particular reaction temperature chosen is related to the type of catalyst used. Certain catalysts will operate effectively at as low as 400° F., whereas others require temperatures above 600° F. to operate satisfactorily. The lower temperatures favor methanol in the equilibrium according to the reaction:

$$CO + 2H_2 \rightarrow CH_3OH. \tag{1}$$

However, the lower temperatures are less favorable for the equilibrium toward carbon monoxide according to the reverse shift reaction which is necessary to produce methanol from carbon dioxide:

$$CO_2 + H_2 \rightarrow CO + H_2O. \tag{2}$$

In view of these two considerations of chemical equilibrium, it is an object of this invention to utilize the characteristics of more than one catalyst and operate over a wide range of temperature conditions favorable for both the above reactions to occur.

It will be noted that the two preceding reactions are not the only ones which occur when the process is carried out. Thus, in the case where the carbon oxide in the makeup feed is all carbon monoxide, the gas contacting the catalyst will react to form small amounts of by-products, such as dimethyl ether and higher alcohols, with the formation of water vapor. For instance, in the case of dimethyl ether, $$2CO + 4H_2 \rightarrow CH_3OCH_3 + H_2O, \tag{3}$$

and in the case of any of the four butyl alcohols, $$4CO + 8H_2 \rightarrow C_4H_9OH + 3H_2O \tag{4}$$

The water vapor produced in (3) or (4) will react by the reverse of reaction (2) to form some carbon dioxide to an extent limited by the chemical equilibrium of the reaction mixture.

It should also be noted that higher pressures favor the equilibrium of reaction (1) and higher temperatures favor reaction (2).

In addition to the chemical equilibrium considerations, the catalysts selected are arranged in a sequence which will minimize the inlet temperature to the first bed, thereby requiring less heat-exchange to heat the gases to the proper temperature for the reaction to initiate.

Furthermore, since the gases pass over catalysts at successively higher temperatures, then are cooled, and then pass into one or more catalyst beds at lower temperature, the following beneficial results are achieved:

The $CO_2$ in the synthesis gas is reverse-shifted to CO under equilibrium conditions at the highest temperature in the last stage of the first reactor sequence. As pointed out previously, this reverse-shift is favored because (a) some CO has already been converted to methanol, because (b) the reaction temperature is higher, and finally because (c) a catalyst specifically capable of promoting the shift of $CO_2$ plus $H_2$ to CO plus $H_2O$, is present in this bed. The gases with increased CO content and reduced $CO_2$ content are now cooled to low temperature where the methanol equilibrium is favored and a catalyst specific for methanol synthesis is employed in this first stage following the initial sequence of beds.

It is also noteworthy that reaction (1) is exothermal whereas reaction (2) is endothermal, so that there is a balancing of temperature effects in the higher temperature beds, tending to make the reactor more nearly isothermal, which also favors efficiency of operation, i.e., minimizes formation of by-products.

By the use of this invention, capital costs and maintenance costs are decreased for a plant of a given capacity because of a significant decrease in the quantity of gas circulated for each unit of methanol produced. The sizes, and therefore the costs, of the circulation compressor, piping, heat-exchangers, and liquid-gas separator in the synthesis "loop" are substantially reduced, in comparison with existing processes with their higher circulating rates.

BACKGROUND OF THE INVENTION

The reaction of hydrogen and one or more carbon oxides to produce methanol produces considerable heat, resulting in an increase in the temperature of the stream of gas being processed. For efficient operation, however, it is essential that the reaction temperature be rather closely controlled. This has been accomplished in the past by using a direct cold gas quench. Note U.S. Pat. No. 3,254,967 to T. O. Wentworth and U.S. Pat. No. 3,480,407 to T. O. Wentworth and C. G. Anderson. Such operations have been carried out using a catalyst having a single composition.

DETAILED DESCRIPTION

Figure 1:
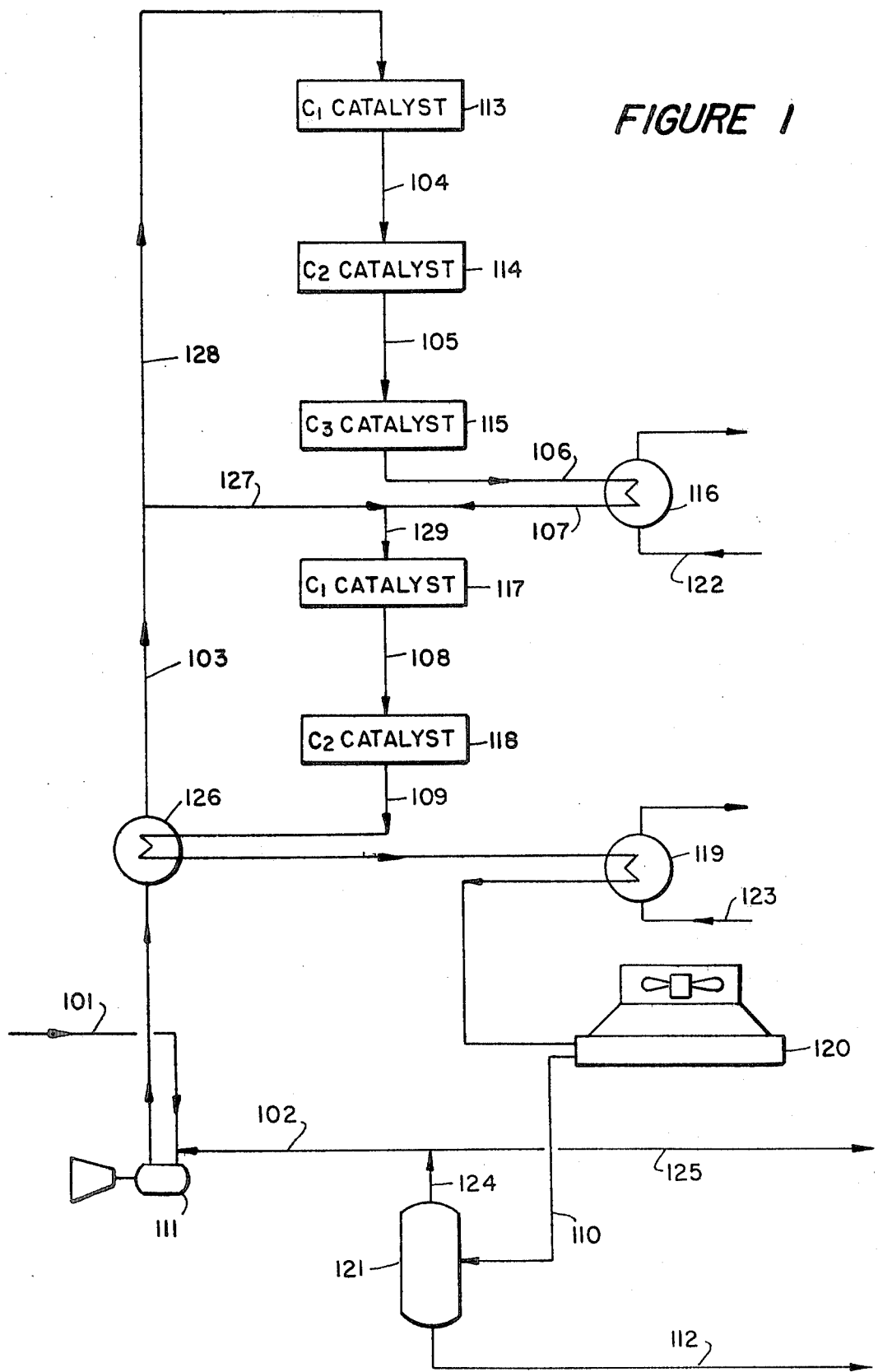

Essentially, the improvements of the present invention with respect to capital costs and operating costs are the result of two changes in conventional methanol synthesis processes. In the first place, in the present process, indirect heat-exchange is employed for the purpose of recovering heat of reaction. In the second place, the present process utilizes two or more different catalyst compositions capable of operating within certain temperature ranges. These catalysts are known in the art. Note Emmett, Catalysis, Volume III (1955—pages 364–377) and Kirk-Othmer, Encyclopedia of Chemical Technology, Second Edition, Volume 13 (1967—page 379).

The process of this invention is one in which the synthesis gas is initially contacted with two or more beds of catalyst arranged in series. These beds of catalyst, in the direction of flow of the gas, are of such composition as to function most efficiently at increasingly higher temperatures. The first bed of catalyst is one which produces methanol at a low initial reaction temperature, thereby minimizing the amount of heat-exchange required to heat the inlet gas to a temperature appropriate for the synthesis reaction to initiate and also taking advantage of the more favorable equilibrium of equation (1) at lower temperatures. The last bed of catalyst in the first sequence of catalyst beds is one which operates at a high temperature, thereby taking advantage of the reverse-shift reaction of equation (2). Preferably, the gas entering the first bed is at a temperature within the range from 400° F. to 500° F. and is at a pressure of from 1000 psi to 7500 psi. Preferably also, the gas exiting the last bed is at a temperature within the range from 700° F. to 750° F. and is also at a pressure of from 1000 psi to 7500 psi. Throughout this specification, "psi" means pounds per square inch gage pressure.

The gaseous stream undergoing reaction, after exiting the last bed mentioned in the preceding paragraph, is cooled by indirect heat-exchange and is then introduced into at least one further bed of catalyst where the temperature remains relatively low. By operating in this manner, advantage is taken of the favorable equilibrium of equation (1) at lower temperatures. Carbon monoxide, including that produced in and exiting from the last bed mentioned in the preceding paragraph, is thereby converted to an increased extent to methanol. Here again, if more than one bed of catalyst is present after the indirect heat-exchange step, the beds are arranged in series, and the beds are of such catalyst composition as to function at increasingly higher temperatures in the direction of flow of the reaction stream. The temperature of the reaction mixture leaving the last bed after the indirect heat-exchange step will range from the temperature of the gas introduced into the first bed of catalyst mentioned in the preceding paragraph to the temperature of the gas exiting the bed immediately preceding the heat-exchange step. Preferably, the temperature of the gas entering the first bed after the heat-exchange step will be within the range from 400° F. to 500° F. and the temperature of the gas leaving the last bed after the heat-exchange step will be within the range from 550° F. to 650° F., or even lower than 550° F.

The process of this invention also includes one in which the gas leaving the last bed after the heat-exchange step mentioned in the preceding paragraph is cooled by indirect heat-exchange and is then introduced into at least one further bed of catalyst. Here again, advantage is taken of the favorable equilibrium of equation (1) at lower temperatures. If more than one bed of catalyst is used after the second heat-exchange step, the beds are arranged in series, and the beds are of such catalyst composition as to function at increasingly higher temperatures in the direction of flow of the reaction stream. The temperature of the reaction mixture leaving the last bed after a second heat-exchange step will range between the temperature of the gas introduced into the first bed of catalyst mentioned in the second preceding paragraph and the temperature of the gas exiting the bed immediately preceding the second heat-exchange step. Preferably, the temperature of the gas entering the first bed after the second heat-exchange step will be within the range from 400° F. to 500° F. and the temperature of the gas leaving the last bed after the second heat-exchange step will be within the range from 500° F. to 550° F.

In one preferred aspect, the process of this invention is one in which the synthesis gas is passed through three (first, second and third) beds of catalyst, is then cooled by indirect heat-exchange, and is then passed through two more (fourth and fifth) beds of catalyst.

The first bed of catalyst is initially contacted at a temperature within the range from 400° F. to 500° F. The first bed is composed of catalyst which functions over temperatures within the range from 400° F. to 550° F. to produce methanol from hydrogen and carbon monoxide. The second bed is composed of catalyst which functions over temperatures within the range from 500° F. to 630° F. to produce methanol from hydrogen and carbon monoxide. As carbon monoxide is converted to methanol in the first and second beds, the reverse shift reaction of equation (2), particularly if a suitable catalyst is present, converts carbon dioxide to carbon monoxide, making more carbon monoxide available to react to form methanol.

Continuing this preferred aspect, the third bed is composed of catalyst which functions over temperatures within the range from 600° F. to 750° F. to produce methanol from hydrogen and carbon monoxide. These higher temperatures promote more reverse shift to produce more carbon monoxide from dioxide. Catalysts suitable for each of the above services will be more fully described hereinafter.

Still continuing this more specific aspect, the effluent from the third bed of catalyst is passed in indirect heat-exchange relationship with a cooling medium (suitably, boiler feed water) whereby the temperature of the effluent is reduced to a temperature within the range from 400° F. to 500° F. If desired, a part of the purified and preheated synthesis gas enters the fourth bed of catalyst without passing through the first three beds of catalyst.

Still continuing this more specific aspect, the effluent from the heat-exchanger is introduced into a fourth bed of catalyst which functions over temperatures within the range from 400° F. to 550° F. to produce methanol from hydrogen and carbon monoxide. This catalyst is preferably the same as that employed in the first bed of the first sequence of reactor beds.

Finally, with respect to this more specific aspect, the effluent from the fourth bed of catalyst is introduced into a fifth bed of catalyst which functions over temperatures within the range of 500° F. to 650° F. to produce methanol from hydrogen and carbon monoxide. This catalyst is preferably the same as that employed in the second bed of the first sequence of reactor beds.

The temperature out of the fifth bed is from 550° F. to 650° F. and is much lower than the temperature out of the third bed (700° F. to 750° F.) (in the first sequence of converter beds and prior to heat exchange and gas cooling), thus allowing the concentration of the methanol out of the fifth bed to reach 7.5 mol percent at 35 percent of methanol equilibrium.

DESCRIPTION OF CATALYSTS

The invention preferably requires the use of at least three general types or classes of catalysts, all known to the art, but for the first time this knowledge is being applied to a new method for methanol synthesis. These catalysts are hereinafter designated as C-1, C-2 and C-3 (also at times hereinafter, respectively, as $C_1$, $C_2$, and $C_3$), but should be considered not as individual catalysts but as classes of catalysts which will perform as required in each service and which differ from each other primarily in the temperature range that each is most suitable for. There is some over-lapping of temperatures that each class of catalysts is capable of functioning in, but despite this over-lap each class should be considered as distinct.

In general, all of the catalysts must be capable of the following: The catalyst class must initiate the reaction at the lowest temperature of the range indicated; for example, for Class C-1 the catalyst must initiate the reaction at 350° F. and be stable and effective to temperatures as high as 540° F. Class C-2 has the same requirements but for a temperature range of 475° F. to 625° F., whereas class C-3 has the range of 575° F. to above 740° F.

All catalysts in all classes should have the following characteristics: They should be tolerant to poisons such as sulfur and halide, or they should be so adsorptive that they will remove the poisons in the upstream portion of the catalyst bed and thus protect the downstream portion for normal action. Most catalysts containing copper and zinc are highly adsorptive of these poisons, whereas these metals can be made tolerant to these same poisons by converting the copper and zinc to such "salts" as chromites ($CuCr_2O_4$), for example, or by the incorporation of such acidic or amphoteric oxides as ceria, mixed rare earth oxides, alumina, titania, zirconia, lanthana, thoria, and combinations of oxides, such as magnesium aluminate spinels and the like. The latter have the further effect of introducing an incipiently isometric nucleus into the catalytic structure. These oxides can be incorporated by co-precipitation of nitrate salts using ammonium hydroxide, ammonium bicarbonate, ammonium carbonate, sodium carbonate or bicarbonate, oxalate, and other alkali satls of these precipitants. It is preferable that the oxides named above be finely divided (thus co-precipitation is the preferred method for introducing them), but some beneficial effect can be obtained by intensively and intimately grinding together the finely divided oxides of, for example, copper oxide, zinc oxide and ceria. Other methods will be evident to the one skilled in the art.

The catalysts should also be resistant to exposure to the temperatures employed. The catalysts should be capable of sustaining their performances for months or even years, so that the slow growth in crystal size which attends some forms of catalyst deactivation is forestalled, even at temperatures slightly above operating range, because there may be operating upsets which cause temperature excursions above the normal operating range. The agents which make the catalysts resistant to the temperature and time effect are essentially the same as those added above to attain poison resistance. Thus, it is desirable to choose a component of the catalyst which will have the dual effect of imparting both poison and temperature resistance. Essentially all of the above mentioned additives do so, but of particular effectiveness are chromia, ceria, mixed rare earth oxides and zirconia. This is not to say that some benefit is not obtained with the others mentioned such as alumina, magnesium aluminate spinel and titania.

The metals comprising the catalysts themselves are as follows:

C-1 is comprised primarily of copper and zinc as the oxides with the copper being in the atom ratio of 1 to more than 6 to each zinc (i.e., 1:1 Cu to Zn to 6:1 Cu to Zn). These, as stated above, can be derived from the nitrate salts and precipitated with the precipitants already mentioned and stabilized with the stabilizers as also described above. The stabilizers can be in the proportion of one to 60 or even more percent, based on the total weight of copper, zinc and stabilizer oxides.

C-2 is also comprised of copper and zinc as the oxides, but with an atom ratio of copper to zinc of 1 to 0.25. This C-2 catalyst can also be different from C-1 in that can include some manganese (particularly if higher alcohols are desired), and can also include a higher quantity of thermal stabilizers. Because of the higher temperature of operation, the thermal stabilizer content is preferably in a range approaching 20% to as high as 65%, or even higher, based on the total weight of copper, zinc and stabilizer oxides.

C-3 is ordinarily zinc chromite, but may contain copper oxide as such or as chromite. This catalyst group may also contain manganese, particularly if higher alcohols are desired as a significant fraction of the product. The further requirement of this catalyst, as explained in the specification above, is that it be effective in the conversion of $CO_2$ and $H_2$ to CO and water vapor. This is achieved either by the incorporation into the catalyst composition or as a component of a mixed charge of catalyst of such very effective catalysts as a copper oxide - zinc oxide catalyst containing the copper in an atom ratio of 1:2 to the zinc. This catalyst can thus conveniently be copper-zinc chromite having a ratio of 1:2:3 Cu:Zn:Cr and can be made by precipitation from the nitrates of copper and zinc in the presence of chromic acid. Precipitation is effected with ammonium hydroxide or other precipitants known to one skilled in the art (ammonium chromate or ammonium carbonate, for example).

All catalysts must be converted to a useable form, which ordinarily means calcining to the oxides, densification, pelleting as one-quarter by one-quarter inch right cylinders, and finally reducing either in the methanol converter, or separately, and then charging in a completely reduced or partially reduced condition. Prior to reducing, the pellets can under some circumstances be calcined in air at temperatures approaching 900° F. to make them less susceptible to spalling and disintegration during reduction and handling.

The catalyst will preferably be distributed in the beds or trays in such a way that the same temperature rise is experienced in each bed or tray: this basically means that the amount of reaction or conversion (productivity) is equal in each bed. Thus, if there are five beds or trays, 20% of the total reaction is effected in each.

The quantity of catalyst may not and very likely will not be equal in weight or volume in each bed. For example, the first bed or converter does not need as much catalyst as the final bed, because the reaction driving force in the first bed where there is little methanol will be greatest, whereas in the last bed the driving force is lowest and the volume of catalyst would be greatest. Generally, the catalyst will increase in quantity from bed to bed in the first sequence of reactors, because the catalysts are intentionally designed to have equal productivity at equal pressures but at incrementally higher temperatures in the order $C_1$, $C_2$, and $C_3$. This is illustrated in the following generalized statement:

Productivity of $C_1$ at $P_1$ and $T_1$ equals
Productivity of $C_1$ at $P_1$ and $T_1+100°$ F. equals
Productivity of $C_3$ at $P_1$ and $T_1+200°$ F.

As the partial pressure of methanol increases, the effect is that $P_1$ is as a consequence reduced as the catalyst "sees" it or responds to it. This same effect pertains for all beds in all sequences. This is illustrated subsequently in the Examples.

Gas Purification

It is recognized that it is a requirement for the mopst efficient operation of a modern methanol plant to have the gas streams pure and free of sulfur, halide, volatile solids and other poisons, both chemical and physical. This is usually accomplished in the gas processing operation, but is not completely effective despite great care in process and engineering design. It is included in this improved methanol process to incorporate additional scavengers and adsorbents in the purification train. This procedure entails either the use of adsorbents having the general composition of the most sensitive catalysts (low temperature catalysts) but with modified physical design or special adsorbent compositions. When the adsorbents are to be employed upstream in the first stage reactor, the adsorbent should be of the same general composition as the catalyst. The improved physical design entails increased porosity and improved availability of the adsorbent entity. This is accomplished by distributing the adsorbent composition on a porous inert support or by designing the composition so that there are many large access pores. This can be accomplished by having present a volatile or combustible solid as fibers or grains in the adsorbent in its final physicl form. It is apparent that a spent catalyst can be reprocessed for use in the adsorbent role, and its location can be either in the reactor itself upstream from the catalyst bed proper or in a separate upstream vessel. Spent (used) catalyst can sometimes be made useful by rigorous screening or tumbling to expose new and fresh adsorptive surfaces.

Avoidance of Metals, Carbonyl Formation and Subsequent Decomposition on the Catalyst One of the major problems in the synthesis of methanol that has been little recognized and probably never compensated for is the problem relating to the formation of metal carbonyls in the high pressure, low temperature portions of the methanol plant where the gas containing carbon monoxide can be in contact with metals forming carbonyls. These metals are commonly iron and nickel which are common materials of construction because of their strength and corrosion resistance (stainless steels). At elevated pressure (above 50 psi) and low temperatures (below 200° C.), the carbon monoxide will react with iron or nickel to form volatile iron or nickel carbonyl. These migrate to the hotter sections of the methanol synthesis "loop", where they deposit as highly active forms of elemental, sponge nickel or iron (or other carbonyl-forming metal). Usually, this is in the catalyst bed and usually on the surface of the catalyst, where the most catalytic damage cn be done. These metals, unlike the methanol synthesis catalyst, form methane, a very undesirable side reaction, from the carbon monoxide and hydrogen synthesis gas. These metals also can form waxes, which deactivate the methanol catalyst and consequently are as severe a poison as the aforementioned sulfur, halides and physicl poisons. To avoid the formation of the carbonyls, it is required that the synthesis gas at elevated pressures and low temperatures contact surfaces which are incapable of forming metallic carbonyls. The surfaces which are to contact the synthesis gas (carbon monoxide, specifically) must therefore be copper, zinc, cadmium, brass, gold, silver, polytetraflorethylene, polypropylene, polyacetal, polycarbonate and similar impervious and tough plastics or non-carbonyl forming metals. Copper lining, or galvanizing the interior of the piping and exposed surfaces, or silver or gold plating them, or plating them with a thin and impervious film of the enumerated plastics, is satisfactory. Impervious lacquers or paints also are adequate if sufficiently temperature and abrason resistant.

REFERENCE TO DRAWINGS

FIGS. 1, 2, 3, 4, 5, 6 and 7 of the drawings are to be considered in connection with Examples 1, 2, 3, 4, 5, 6 and 7, respectively. Examples 1, 3, 5, 6 and 7 are embodiments of this invention. Examples 2 and 4 are not embodiments of this invention, but are included by way of comparison. Examples 1 and 2 relate to operations in which the synthesis gas is prepared from natural gas, and Examples 3, 4, 5, 6 and 7 relate to operations in which the synthesis gas is prepared by the gasification of coal. Those skilled in the art will understand that the present invention is independent of the source of the raw material used in preparing the synthesis gas, which preferably will be composed of at least two-thirds carbon monoxide by volume, based upon the total volume of carbon monoxide and carbon dioxide. For further information concerning the preparation of synthesis gas, note Kirk-Othmer, Encyclopedia of Chemical Technology, Second Edition, Volume 13 (1967—pages 381-384). Examples 8, 9 and 10 respectively describe the preparation of $C_1$, $C_2$, and $C_3$ catalyst. Example 11 describes the preparation of scavengers for trace poisons which may be present in the synthesis gas.

EXAMPLE 1

This example describes an embodiment of the present invention in which the synthesis gas is derived from natural gas and is to be considered in conjunction with FIG. 1 of the drawings and Table I. FIG. 1 depicts a synthesis loop and Table I gives the compositions of various streams shown in FIG. 1. In Table I, "I" signifies inerts and "M/T" signifies pound moles per short ton of methanol. It is to be understood that methanol synthesis "loops" can vary widely in capacity, for example, from 500 short tons per day to as large as 15,000 short tons per day of methanol product from a single synthesis train. It is further understood that the greater the capacity the higher the optimized loop pressure will be.

TABLE I

| STR | 101 | | 102 | | 103 | |
|---|---|---|---|---|---|---|
| COMP | M/T | % | M/T | % | M/T | % |
| $H_2$ | 184.93 | 69.31 | 514.11 | 69.60 | 699.04 | 69.51 |
| CO | 43.54 | 16.32 | 76.11 | 10.30 | 119.65 | 11.90 |
| $CO_2$ | 31.95 | 11.97 | 52.09 | 7.05 | 84.04 | 8.36 |
| I | 6.41 | 2.40 | 93.39 | 12.64 | 99.80 | 9.93 |
| MEOH | | | 3.10 | 0.41 | 3.00 | 0.30 |
| TOTAL | 266.83 | 100.00 | 738.80 | 100.00 | 1005.53 | 100.00 |

| STR | 109 | | 112 | 125 |
|---|---|---|---|---|
| COMP | M/T | % | M/T | M/T |
| $H_2$ | 549.31 | 62.40 | 2.13 | 33.27 |
| CO | 81.35 | 9.24 | 0.46 | 4.78 |
| $CO_2$ | 59.73 | 6.79 | 4.34 | 3.30 |
| I | 99.80 | 11.33 | 0.57 | 5.84 |
| MEOH | 65.81 | 7.48 | 62.50 | 0.21 |
| $H_2O$ | 24.31 | 2.76 | 24.31 | |
| TOTAL | 880.31 | 100.00 | 94.31 | 47.40 |

Referring to FIG. 1, fresh feed (also known as make-up gas) at a pressure of 4200 psi is introduced into the synthesis loop through line 101 and is admixed with recycle gas flowing through line 102. The mixed stream is then pumped by circulating compressor 111 through heat-exchanger 126, wherein the temperture of the gas is raised to 450° F. To produce one short ton of methanol, 52 brake horse power hours is supplied to compressor 111. Stream 103 splits, 78.35% going to stream 128 and 21.65% to stream 127.

Stream 128 then passes through three beds of catalyst $C_1$, $C_2$, and $C_3$ which are located in beds 113, 114 and 115. The temperature of the gas leaving bed 113 is 530° F., the temperature of the gas leaving bed 114 is 626° F., and the temperature of the gas leaving bed 115 is 708° F. These temperature increases result from the exothermicity of the reactions occurring in these catalytic reactor beds. $C_1$ is a low temperature methanol synthesis catalyst (prepared as described in Example 8) which functions at a pressure of 1500 psi to 7500 psi specifically in this Example at 4000–4200 psi and at temperatures within the range from about 400° F. to 550° F. to produce methanol from hydrogen and a carbon oxide. $C_2$ is a medium temperature methanol synthesis catalyst (prepared as described in Example 9) which functions at a pressure of 1500 psi to 7500 psi (specifically at 4000–4150 for this Example) and at temperatures within the range from about 500° F. to 630° F. to produce methanol from hydrogen and a carbon oxide. $C_3$ as a high temperature methanol synthesis catalyst (described in Example 10) which functions at a pressure of 1500 psi to 7500 psi (specifically 4000–4150 for this example), and at temperatures within the range from about 600° F. to 750 ° F. to produce methanol from hydrogen and a carbon oxide.

The effluent from reactor 115 flows through line 106 and through indirect heat-exchanger 116 wherein the effluent is cooled by means of indirect heat-exchange with boiler feed water introduced through line 122. After having passed through heat-exchanger 116, the effluent is at a temperture of 474° F. and then mixes with stream 127.

The mix is introduced into bed 117, initially contacting a bed of $C_1$ catalyst and then a bed 118 of $C_2$ catalyst, the compositions of which are taught in Examples 8 and 9, respectively.

The effluent from bed 118 passes through line 109 and is at a temperature of 618° F. The stream in line 109 contains 7.48 percent methanol on a molar basis. At equilibrium, the stream would have contained 21.69 mole percent methanol. The reaction to produce methanol approaches equilibrium to the extent of 43 percent, based upon the conversion of carbon monoxide, or 35 percent of methanol equilibrium.

Stream 109 is cooled by passage through indirect heat-exchanger 126; by passage through indirect heat-exchanger 119 generating low pressure steam from water introduced by means of line 123; and by passage through air-cooler 120. The process stream exiting cooler 120 is introduced by means of line 110 into separator 121, from the bottom of which liquid methanol product, containing small quantities of dimethyl ether and higher alcohols, admixed with water, is removed through line 112.

A gaseous phase is removed from separator 121 by means of line 124. Part of the stream passing through line 124 is returned into the synthesis loop by means of line 102, and the remainder is purged from the system by means of line 125.

If one assumes a 5,000 short ton per day methanol plant, there would be required approximately 5,000 cubic feet of total catalyst distributed roughly as follows, as an example:

Bed 113, Catalyst $C_1$, volume approximately 500 ft$^3$
Bed 114, Catalyst $C_2$, volume approximately 700 ft$^3$
Bed 115, Catalyst $C_3$, volume approximately 1,500 ft$^3$
Bed 117, Catalyst $C_1$, volume approximately 1,050 ft$^3$
Bed 118, Catalyst $C_2$, volume approximately 1,250 ft$^3$ These are approximate volumes of catalyst and pertain to catalysts of the present art. However, as catalyst improvements are attained the quantities of catalyst in the reactors or trays and the type of distribution can be modified. The benefits to be attained by a more active catalyst are reduced pressure drop and reduced catalyst cost. The catalyst would ordinarily be one-fourth inch by one-fourth inch right cylinders, but other sizes and shapes may be preferred under certain circumstances. The catalyst volume increases in successive downstream beds in each sequence of reactors because the methanol partial pressure increases and, as previously explained, catalysts are designed for essentially equivalent productivity at equal pressures but at incrementally higher temperatures in the order $C_1$, $C_2$, and $C_3$. Because of the increasing partial pressure of methanol, the catalyst volume must be increased to compensate for the decreased "driving force" for the reaction.

EXAMPLE 2

This Example is to be compared with Example 1. In this Example 2, which is not an embodiment of the present invention, the reaction temperature is controlled solely by means of the prior art, direct cold gas quench, no indirect heat-exchange being used to control the reaction temperature.

Figure 2:
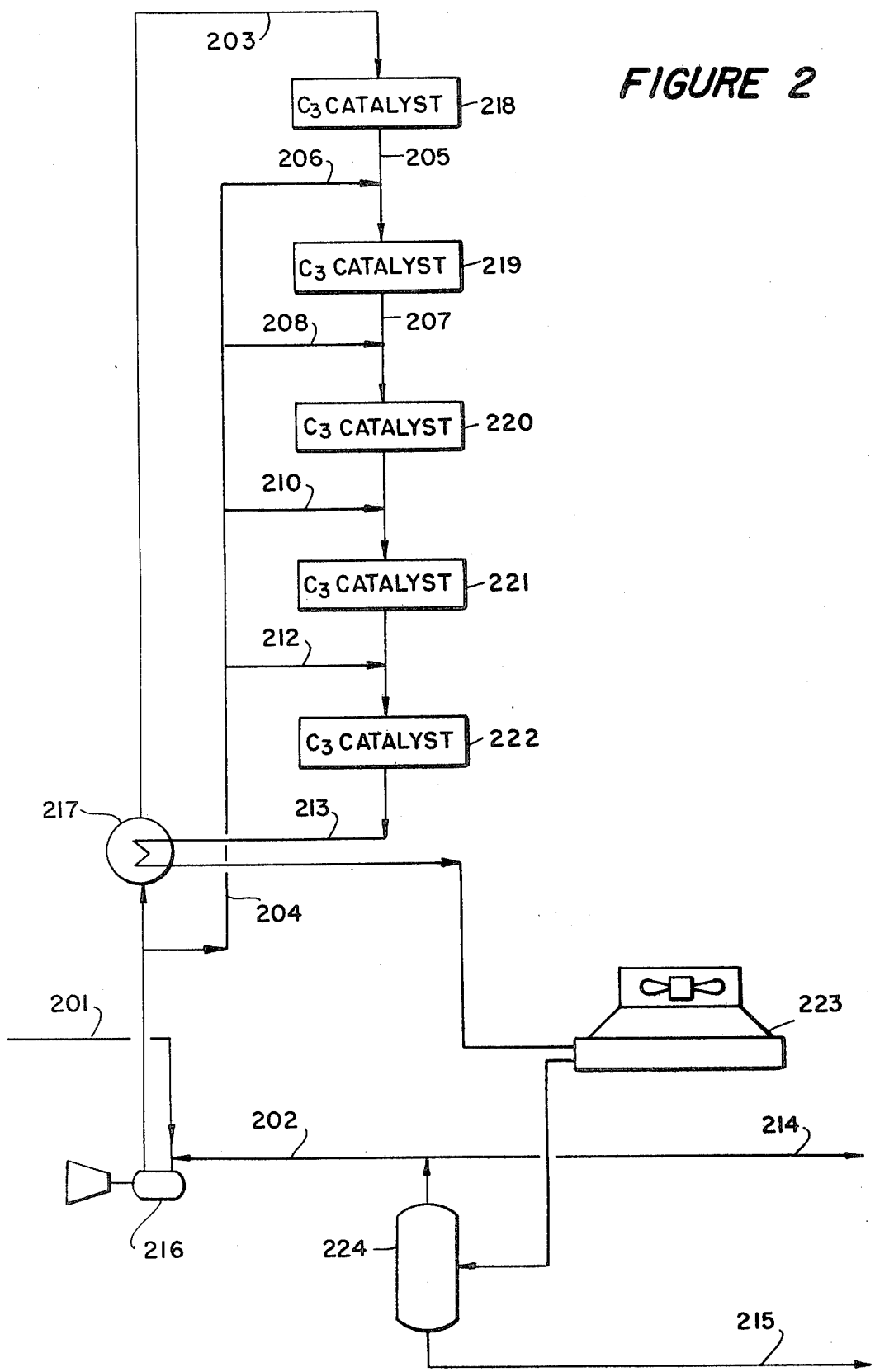

This example is to be considered in conjunction with FIG. 2 of the drawings and Table II. FIG. 2 depicts a synthesis loop and Table II gives the compositions of various streams shown in FIG. 2.

TABLE II

| STR | 201 | | 202 | | 203 | |
|---|---|---|---|---|---|---|
| COMP | M/T | % | M/T | % | M/T | % |
| $H_2$ | 189.94 | 71.07 | 1106.62 | 73.90 | 1012.06 | 73.38 |
| CO | 40.34 | 15.10 | 130.18 | 8.71 | 133.30 | 9.67 |
| $CO_2$ | 30.67 | 11.40 | 51.64 | 3.44 | 64.36 | 4.67 |
| I | 6.49 | 2.43 | 203.28 | 13.55 | 164.00 | 11.95 |
| MEOH | | | 5.88 | 0.40 | 4.59 | 0.33 |
| TOTAL | 267.44 | 100.00 | 1497.60 | 100.00 | 1378.31 | 100.00 |

| STR | 204 | | 205 | | 206 | 207 | 208 |
|---|---|---|---|---|---|---|---|
| COMP | M/T | % | M/T | % | M/T | M/T | M/T |
| $H_2$ | 284.50 | 73.38 | 975.31 | 53.39 | | 995.00 | 77.14 |
| CO | 37.22 | 9.67 | 130.15 | 6.99 | | 131.84 | 10.10 |
| $CO_2$ | 17.95 | 4.67 | 54.21 | 3.38 | | 49.89 | 4.86 |
| I | 45.77 | 11.95 | 164.00 | 8.60 | | 172.60 | 12.41 |
| MEOH | 1.29 | 0.33 | 17.89 | 0.24 | | 31.13 | 0.35 |
| $H_2O$ | | | 10.15 | | | 17.85 | |
| TOTAL | 386.73 | 100.00 | 1351.71 | 72.60 | | 1398.31 | 104.86 |

| STR | 209 | 210 | 211 | 212 | 213 | | 214 | 215 |
|---|---|---|---|---|---|---|---|---|
| COMP | M/T | M/T | M/T | M/T | M/T | % | M/T | M/T |
| $H_2$ | 1042.44 | 81.48 | 1093.87 | 72.49 | 1144.28 | 69.73 | 35.40 | 2.26 |
| CO | 133.54 | 10.67 | 134.66 | 9.46 | 134.73 | 8.22 | 4.16 | 0.39 |

TABLE II-continued

| | | | | | | | | |
|---|---|---|---|---|---|---|---|---|
| $CO_2$ | 50.45 | 5.14 | 51.94 | 4.57 | 55.41 | 3.38 | 1.65 | 2.12 |
| I | 185.01 | 13.11 | 198.12 | 11.65 | 209.77 | 12.85 | 5.88 | 0.61 |
| MEOH | 44.18 | 0.37 | 57.75 | 0.33 | 68.57 | 4.18 | 0.19 | 62.50 |
| $H_2O$ | 22.15 | | 25.80 | | 26.90 | 1.64 | | 26.90 |
| TOTAL | 1477.77 | 110.77 | 1562.14 | 98.50 | 1639.66 | 100.00 | 47.28 | 94.78 |

In Table II, "I" signifies inerts and "M/T" signifies pound moles per short ton of methanol.

Referring to FIG. 2, fresh feed at a pressure of 4200 psi is introduced into the synthesis loop through line 201 and is admixed with recycle gas flowing through line 202. The mixed stream is then pumped by circulating compressor 216. To produce one short ton of methanol, 89 brake horse power hours is supplied to compressor 216. Part of the stream pumped by compressor 216 flows through indirect heat-exchanger 217 and from there by means of line 203 is introduced into bed 218 at a temperature of 630° F. The remainder of the stream pumped by compressor 216 flows through line 204, which is split into streams 206, 208, 210 and 212. These streams 206, 208, 210 and 212 constitute the direct cold gas quench of the prior art.

Bed 218 contains the $C_3$ catalyst of Example 1. By passage through bed 218, the temperature of the gas is raised to 675° F., and the temperature of the mixed stream entering bed 219 is 650° F.

Bed 219 also contains the $C_3$ catalyst of Example 1. By passage through bed 219, the temperature of the gas is raised to 695° F., and the temperature of the mixed stream entering bed 220 is 660° F.

Bed 220 also contains $C_3$ catalyst of Example 1. By passage through bed 220, the temperature of the gas is raised to 705° F., and the temperature of the mixed stream entering bed 221 is 670° F.

Bed 221 also contains $C_3$ catalyst of Example 1. By passage through bed 221, the temperature of the gas is raised to 715° F., and the temperature of the mixed stream entering bed 222 is 685° F.

Bed 222 also contains the $C_3$ catalyst of Example 1. By passage through bed 222, the temperature of the gas is raised to 720° F. This gas passes by means of line 213 through heat-exchanger 217 and air-cooler 223, and is introduced into separator 224, from the bottom of which liquid methanol product, containing small quantities of dimethyl ether and higher alcohols, admixed with water, is removed through line 215.

The stream in line 213 contains 4.18 percent methanol on a molar basis. At equilibrium, the stream would have contained 10.29 mole percent methanol. The reaction to produce methanol approaches equilibrium to the extent of 45 percent, based upon the conversion of carbon monoxide, or 41 percent of methanol equilibrium.

A gaseous phase is removed from separator 224. Part of this gaseous phase is returned into the synthesis loop by means of line 202, and the remainder is purged from the system by means of line 214.

For a 5,000 short ton per day methanol plant, there would be required approximately 5,000 cubic feet of catalyst, all C-3 type, distributed roughly as follows, as an example:

Bed 218, Catalyst $C_3$, volume approximately 600 ft³
Bed 219, Catalyst $C_3$, volume approximately 700 ft³
Bed 220, Catalyst $C_3$, volume approximately 900 ft³
Bed 221, Catalyst $C_3$, volume approximately 1,200 ft³
Bed 222, Catalyst $C_3$, volume approximately 1,600 ft³

The catalyst would ordinarily be one-fourth inch by one-fourth inch right cylinders, but other sizes and shapes may be preferred under certain circumstances. It is apparent that the catalyst quantities increase in each of the succeeding downstream beds. This is because the reaction temperature remains almost the same in succeeding beds but the methanol partial pressure increases and the residence time must consequently be increased.

EXAMPLE 3

Figure 3:
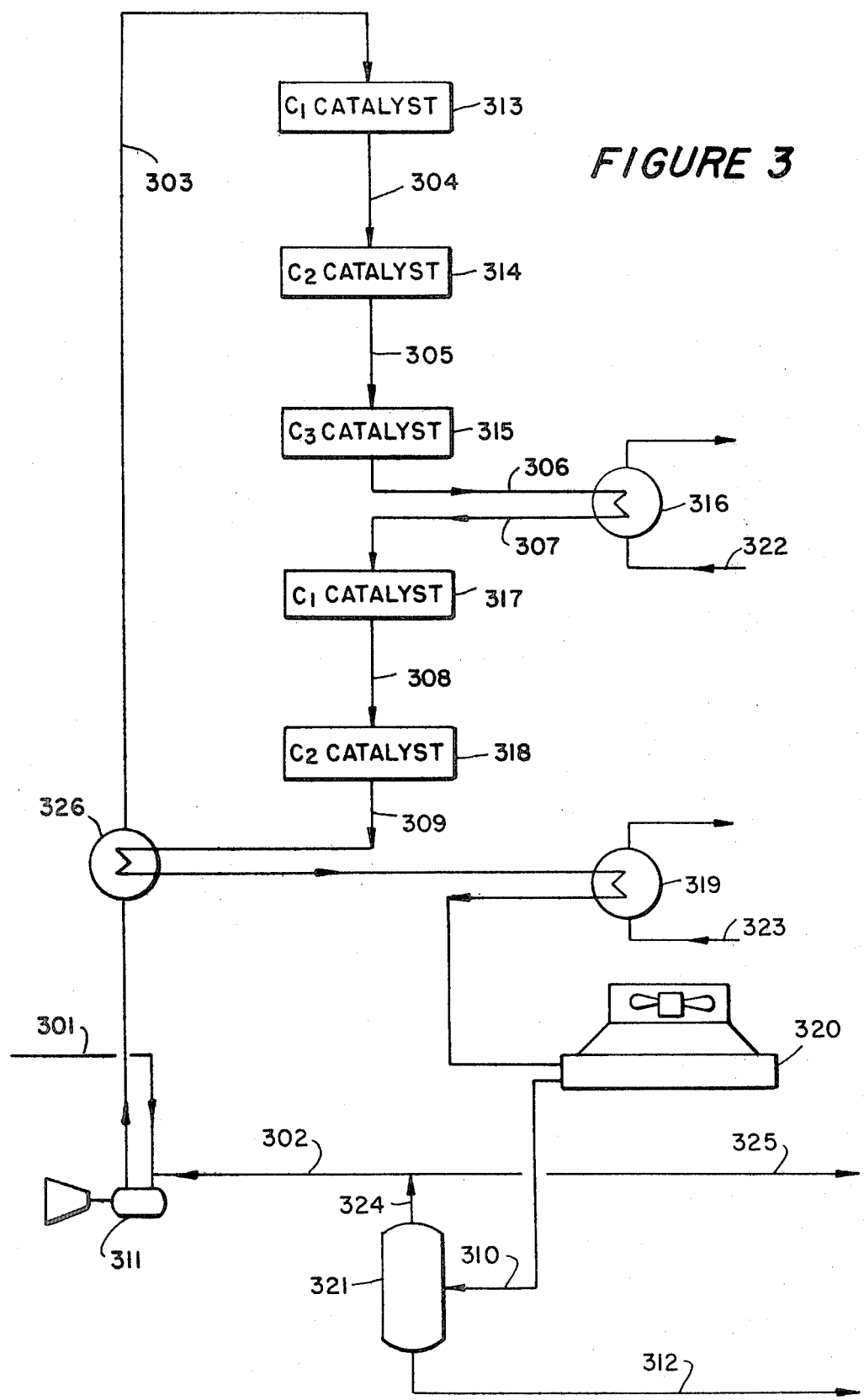

This Example describes an embodiment of the present invention in which the synthesis gas is prepared by the gasification of coal and is to be considered in conjunction with FIG. 3 of the drawings and Table III. FIG. 3 depicts a synthesis loop and Table III gives the compositions of various streams shown in FIG. 3. In Table III, "I" signifies inerts, and "M/T" signifies pound moles per short ton of methanol produced. Here again, it is to be understood that synthesis loops can vary widely in capacity, for example, from 500 short tons per day to as large as 15,000 short tons per day of methanol product.

Referring to FIG. 3, fresh feed at a pressure of 3800 psi is introduced into the synthesis loop through line 301 and is admixed with recycle gas flowing through line 302. The mixed stream is then pumped by circulating compressor 311 through heat-exchanger 326 wherein the temperature of the gas is raised to 450° F. To produce one short ton of methanol, 50 brake horse power hours is supplied to compressor 311.

TABLE III

| STR | 301 | | 302 | | 303 | |
|---|---|---|---|---|---|---|
| COMP | M/T | % | M/T | % | M/T | % |
| $H_2$ | 137.53 | 66.85 | 573.27 | 72.18 | 710.80 | 71.08 |
| CO | 65.24 | 31.71 | 114.16 | 14.37 | 179.40 | 17.94 |
| $CO_2$ | 0.66 | 0.32 | 6.34 | 0.80 | 7.00 | 0.70 |
| I | 2.31 | 1.12 | 97.39 | 12.26 | 99.70 | 9.97 |
| MEOH | | | 3.07 | 0.39 | 3.07 | 0.31 |
| TOTAL | 205.74 | 100.00 | 794.23 | 100.00 | 999.97 | 100.00 |

| STR | 305 | | 306 | | 309 | | 312 | 325 |
|---|---|---|---|---|---|---|---|---|
| COMP | M/T | % | M/T | % | M/T | % | M/T | M/T |
| $H_2$ | 658.36 | 69.48 | 632.36 | 68.62 | 585.70 | 66.94 | 2.37 | 10.06 |
| CO | 153.18 | 16.17 | 140.18 | 15.21 | 116.85 | 13.36 | 0.69 | 2.00 |
| $CO_2$ | 7.00 | 0.74 | 7.00 | 0.76 | 7.00 | 0.80 | 0.56 | 0.10 |
| I | 99.70 | 10.52 | 99.70 | 10.82 | 99.70 | 11.40 | 0.60 | 1.71 |
| MEOH | 29.29 | 3.09 | 42.29 | 4.59 | 65.62 | 7.50 | 62.50 | 0.05 |

TABLE III-continued

| TOTAL | 947.53 | 100.00 | 921.53 | 100.00 | 874.87 | 100.00 | 66.72 | 13.92 |

Stream 303 passes through three beds of catalyst $C_1$, $C_2$ and Chd 3 which are located in beds 313, 314, and 315. The temperature of the gas exiting bed 313 is 530° F., the temperature of the gas exiting bed 314 is 630° F., and the temperature of the gas exiting bed 315 is 720° F. The $C_1$, $C_2$ and $C_3$ catalysts are the same as those described in Example 1.

The stream in line 306 contains 4.59 percent methanol on a molar basis. At equilibrium, the stream would have contained 13.7 mole percent methanol. The reaction to produce methanol approaches equilibrium to the extent of 39 percent, based upon the conversion of carbon monoxide, or 35 percent of methanol equilibrium.

The effluent from bed 315 flows through line 306 and through indirect heat-exchanger 316 wherein the effluent is cooled by means of indirect heat-exchanger with boiler feed water introduced through line 322. After having passed through heat-exchanger 316, the effluent is at a temperature of 450° F.

The effluent is then introduced into bed 317, initially contacting a bed of $C_1$ catalyst and then a bed, 318, of $C_{12}$ catalyst, those catalysts having been defined in Example 1.

The effluent from bed 318 passes through line 309 and is at a temperature of 600° F. The stream in line 309 contains 7.50 percent methanol on a molar basis. At equilibrium, the stream would have contained 25.5 mole percent methanol. The reaction to produce methanol approaches equilibrium to the extent of 39 percent, based upon the conversion of carbon monoxide, or 29 percent of methanol equilibrium.

Stream 309 is cooled by passage through indirect heat-exchanger 326, by passage through indirect heat-exchanger 319, generating low pressure steam from boiler feed water introduced by means of line 323, and by passage through air cooler 320. The process stream exiting cooler 320 is introduced into separator 321, from the bottom of which liquid methanol, containing small quantities of dimethyl ether and higher alcohols and which is almost anhydrous, is removed through line 312.

A gaseous phase is removed overhead from separator 321 through line 324 and split into streams 302 and 325. Stream 302 is returned into the synthesis loop, whereas stream 325 is purged.

If one assumes a 5,000 short ton per day methanol plant, there would be approximately 5,000 cubic feet of catalyst distributed roughly as follows: It will be noted that the conditions pertaining for Example 3 are very similar to those pertaining for Example 1, except for synthesis gas raw materials (natural gas vs. coal), and as a result the catalyst distribution will be the same.

Bed 313, Catalyst $C_1$, volume approximately 500 ft$^3$
Bed 314, Catalyst $C_2$, volume approximately 700 ft$^3$
Bed 315, Catalyst $C^3$, volume approximately 1,500 ft$^3$
Bed 317, Catalyst $C_1$, volume approximately 1,050 ft$^3$
Bed 318, Catalyst $C_2$, volume approximately 1,250 ft$^3$ These are approximate volumes of catalyst and pertain to catalysts of the present art. However, as catalyst improvements are attained the quantities of catalyst in the reactors or trays and the type of distribution can be modified. The benefits to be attained by a more active catalyst are reduced pressure drop and reduced catalyst cost.

EXAMPLE 4

This example is to be compared with Example 3. In this Example 4, which is not an embodiment of the present invention, the reaction temperature is controlled solely by means of the prior art, direct cold gas quench, no indirect heat-exchanger being used to control the reaction temperature.

TABLE IV

| STR | 401 | | 402 | | 403 | |
|---|---|---|---|---|---|---|
| COMP | M/T | % | M/T | % | M/T | % |
| $H_2$ | 137.53 | 66.85 | 1152.17 | 72.27 | 913.67 | 71.66 |
| CO | 65.24 | 31.71 | 229.10 | 14.37 | 208.46 | 16.35 |
| $CO_2$ | .66 | .32 | 11.48 | .72 | 8.54 | 0.67 |
| I | 2.31 | 1.12 | 195.77 | 12.28 | 140.25 | 11.00 |
| MEOH | | | 5.74 | .36 | 4.08 | .32 |
| TOTAL | 205.74 | 100.00 | 1594.26 | 100.00 | 1275.00 | 100.00 |

| STR | 404 | | 405 | 406 | 407 | 408 |
|---|---|---|---|---|---|---|
| COMP | M/T | % | M/T | M/T | M/T | M/T |
| $H_2$ | 376.20 | 71.66 | 889.91 | 74.53 | 940.88 | 99.61 |
| CO | 85.83 | 16.35 | 196.58 | 17.00 | 201.8 | 22.73 |
| $CO_2$ | 3.52 | .67 | 8.54 | .70 | 9.24 | .93 |
| I | 57.75 | 11.00 | 140.25 | 11.44 | 151.69 | 15.29 |
| MEOH | 1.68 | .32 | 15.96 | .33 | 28.07 | .44 |
| TOTAL | 524.98 | 100.00 | 1251.24 | 104.00 | 1331.68 | 139.00 |

| STR | 409 | 410 | 411 | 412 | 413 | |
|---|---|---|---|---|---|---|
| COMP | M/T | M/T | M/T | M/T | M/T | % |
| $H_2$ | 1014.55 | 108.92 | 1097.53 | 93.16 | 1164.79 | 69.57 |
| CO | 211.56 | 24.85 | 223.44 | 21.26 | 231.75 | 13.84 |
| $CO_2$ | 10.17 | 1.02 | 11.19 | .87 | 12.06 | .72 |
| I | 166.98 | 16.72 | 183.7 | 14.3 | 198.00 | 11.82 |
| MEOH | 41.48 | .49 | 54.94 | .42 | 68.31 | 4.05 |
| TOTAL | 1444.74 | 152.00 | 1570.80 | 130.01 | 1674.91 | 100.00 |

| STR | 414 | 415 |
|---|---|---|
| COMP | M/T | M/T |
| $H_2$ | 10.06 | 2.37 |
| CO | 2.00 | .69 |
| $CO_2$ | .10 | .56 |
| I | 1.71 | .60 |
| MEOH | .05 | 62.50 |
| TOTAL | 13.92 | 66.72 |

Figure 4:
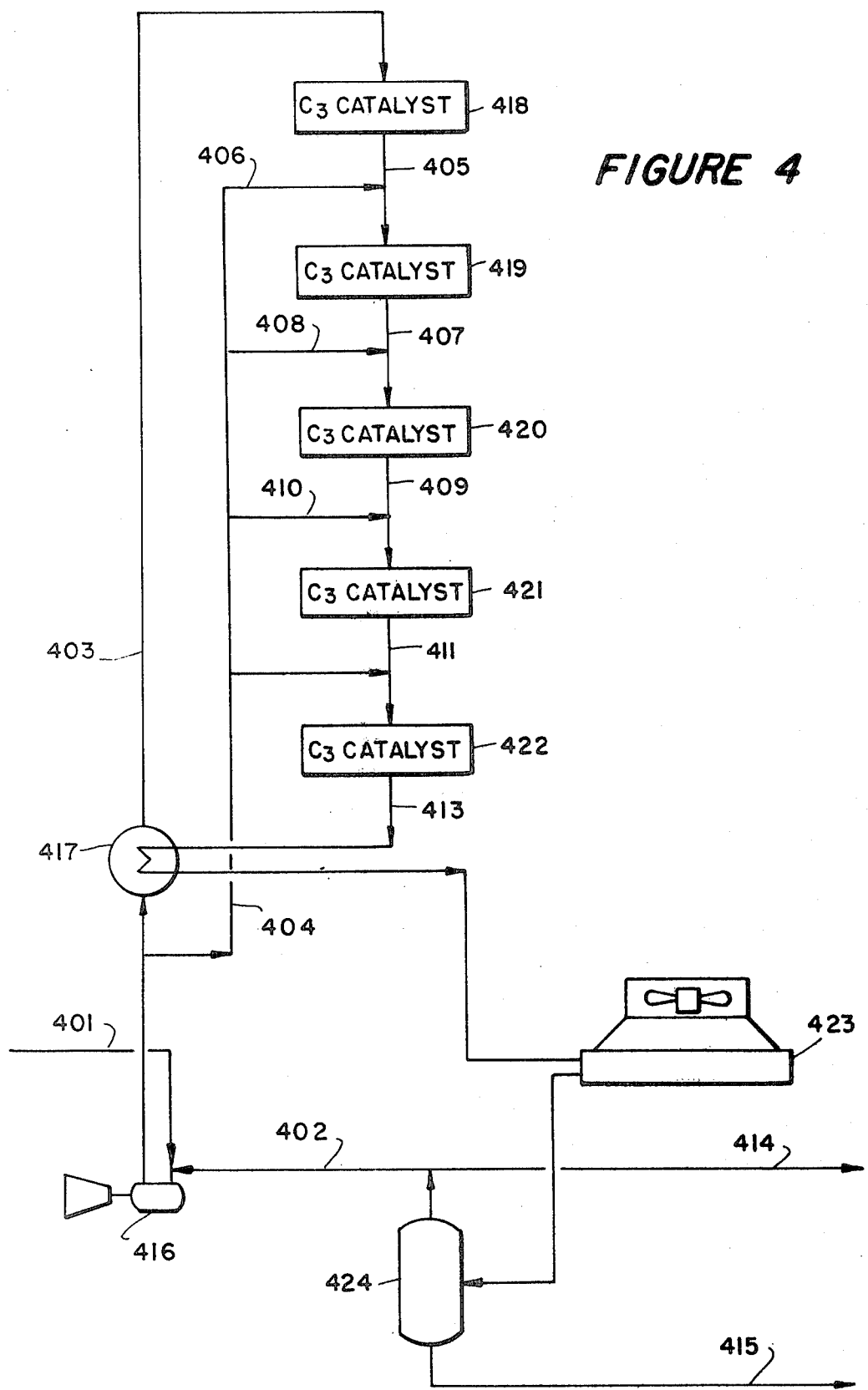

This example is to be considered in conjunction with FIG. 4 of the drawings and Table IV. FIG. 4 depicts a synthesis loop and Table IV gives the compositions of various streams shown in FIG. 4. In Table IV, "I" signifies inerts and "M/T" signifies pound moles per short ton of methanol produced.

Referring to FIG. 4, fresh food at a pressure of 3800 psi is introduced into the synthesis loop through line 401 and is admixed with recycle gas flowing through line 402. The mixed stream is then pumped by circulating compressor 416. To produce one short ton of methanol, 90 brake horse power hours is supplied to compressor 416. Part of the stream pumped by compressor 416 flows through indirect heat-exchanger 417 and from there by means of line 403 is introduced into reactor bed 418 at a temperature of 630° F. The remainder of the stream pumped by compressor 416 flows through line 404, which is split into streams 406, 408, 410 and 412. These streams 406, 408, 410 and 412 constitute the direct cold gas quench of the prior art.

Bed 418 contains the $C_3$ catalyst of Example 1. By passage through bed 418, the temperature of the gas is raised to 680° F., and the temperature of the mixed stream entering bed 419 is 650° F.

Bed 419 also contains the $C_3$ catalyst of Example 1. By passage through bed 419, the temperature of the gas is raised to 700° F., and the temperature of the mixed stream entering bed 420 is 660° F.

Bed 420 also contains the $C_3$ catalyst of Example 1. By passage through bed 420, the temperature of the gas is raised to 710° F., and the temperature of the mixed stream entering bed 421 is 670° F.

Bed 421 also contains the $C_3$ catalyst of Example 1. By passage through bed 421, the temperature of the gas is raised to 720° F., and the temperature of the mixed stream entering bed 422 is 680° F.

Bed 422 also contains the $C_3$ catalyst of Example 1. By passage through bed 422, the temperature of the gas is raised to 720° F. This gas passes by means of line 413 through heat-exchanger 417 and air cooler 423, and is introduced into separator 424, from the bottom of which liquid methanol, containing small quantities of dimethyl ether and higher alcohols and which is almost anhydrous, is removed through line 415.

The stream in line 413 contains 4.05 percent methanol on a molar basis. At equilibrium, the stream would have contained 12.40 mole percent methanol. The reaction to produce methanol approaches equilibrium to the extent of 38 percent, based upon the conversion of carbon monoxide, or 33 percent of methanol equilibrium.

A gaseous phase is removed overhead from separator 424 and is split into streams 402 and 414. Stream 402 is returned into the synthesis loop, whereas stream 414 is purged.

For a 5,000 short ton per day methanol plant, there would be required approximately 5,000 cubic feet of catalyst distributed roughly as follows: It will be noted that the conditions pertaining for Example 4 are very similar to those pertaining for Example 2, except for the synthesis gas raw materials (natural gas vs. coal), and as a consequence the catalyst distribution will be the same.

Bed 418, Catalyst $C_3$, volume approximately 600 ft$^3$
Bed 419, Catalyst $C_3$, volume approximately 700 ft$^3$
Bed 420, Catalyst $C_3$, volume approximately 900 ft$^3$
Bed 421, Catalyst $C_3$, volume approximately 1,200 ft$^3$
Bed 422, Catalyst $C_3$, volume approximately 1,600 ft$^3$

EXAMPLE 5

Figure 5:
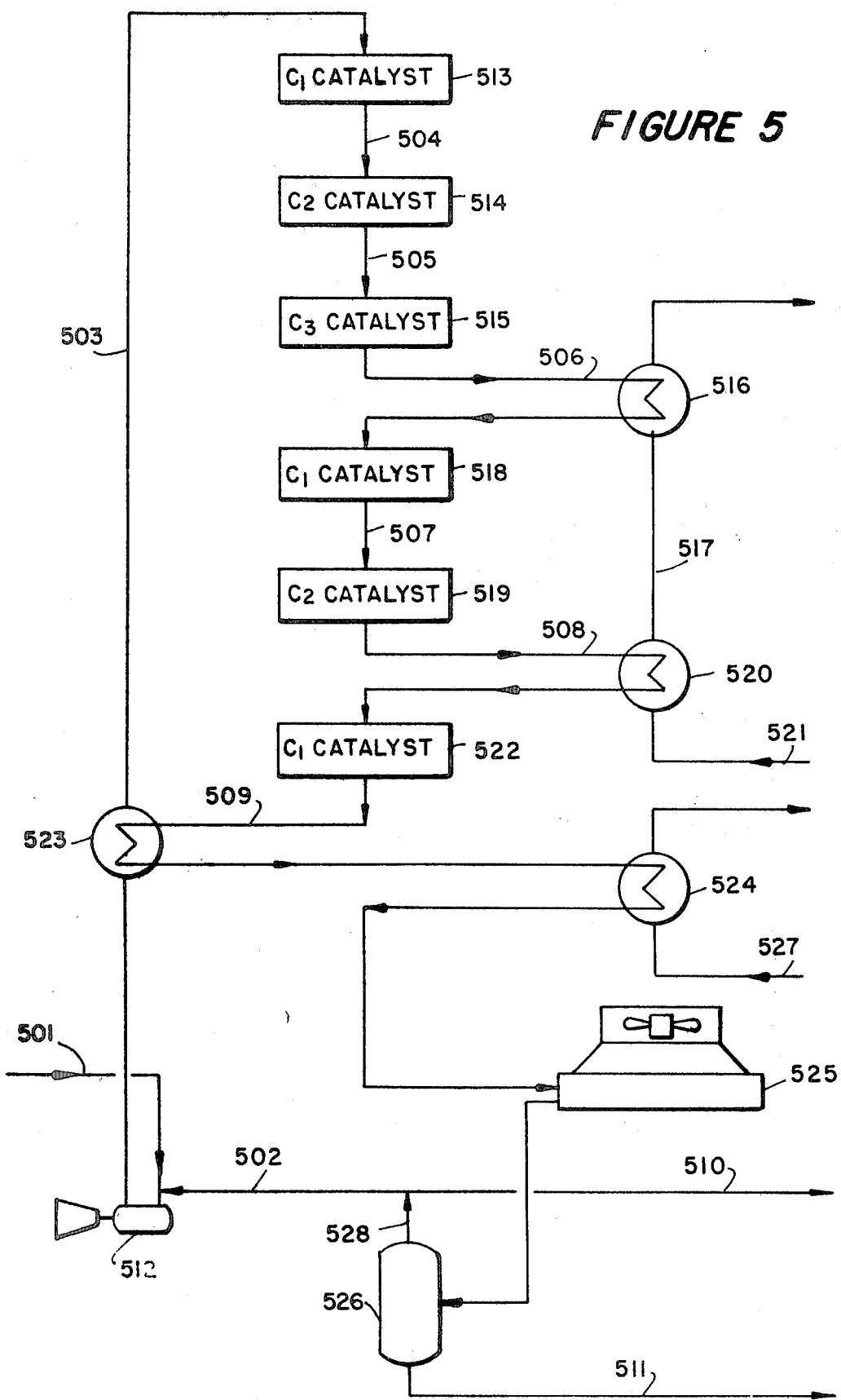

This Example describes an embodiment of the present invention in which the synthesis gas is prepared by the gasification of coal and is to be considered in conjunction with FIG. 5 of the drawings and Table V. FIG. 5 depicts a synthesis loop and Table V gives the compositions of various streams shown in a FIG. 5. In Table V, "I" signifies inerts and "M/T" signifies pound moles per short ton of methanol produced. Here again, it is to be understood that synthesis loops can vary widely in capacity, for example, from 500 tons per day to as large as 15,000 tons per day of methanol product, and that pressures can vary from 750 psi to 7500 psi or even 10,000 psi or above.

Referring to FIG. 5, fresh feed at a pressure 4200 psi is introduced into the synthesis loop through line 501 and is admixed with recycle gas flowing through line 502. The mixed stream is compressed to a pressure of 4500 psi by means of compressor 512. The compressed stream flows through heat-exchanger 523 wherein the temperature of the gas is raised to 400° F. To produce one short ton of methanol 27 brake horse power hours is supplied to compressor 512.

Stream 503 passes through three beds of catalyst $C_1$, $C_2$ and $C_3$, which are located in beds 513, 514 and 515.

TABLE V

| STR | 501 | | 502 | | 503 | | 504 | 505 |
|-----|-----|-----|-----|-----|-----|-----|-----|-----|
| COMP | M/T | % | M/T | % | M/T | % | M/T | M/T |
| $H_2$ | 136.63 | 67.07 | 287.90 | 73.49 | 424.53 | 71.27 | 406.03 | 382.85 |
| CO | 64.40 | 31.50 | 42.07 | 10.76 | 106.47 | 17.88 | 97.22 | 85.63 |
| $CO_2$ | 0.62 | 0.30 | 2.98 | 0.76 | 3.60 | 0.61 | 3.60 | 3.60 |
| I | 2.31 | 1.13 | 57.09 | 14.60 | 59.40 | 9.98 | 59.40 | 59.40 |
| MEOH | | | 1.54 | 0.39 | 1.54 | 0.26 | 10.79 | 22.38 |
| TOTAL | 203.96 | 100.00 | 391.58 | 100.00 | 595.54 | 100.00 | 577.04 | 553.86 |

| STR | 506 | | 507 | 508 | 509 | | 510 | 511 |
|-----|-----|-----|-----|-----|-----|-----|-----|-----|
| COMP | M/T | % | M/T | M/T | M/T | % | M/T | M/T |
| $H_2$ | 363.45 | 68.03 | 344.93 | 321.75 | 299.43 | 63.66 | 9.12 | 2.41 |
| CO | 75.93 | 14.20 | 66.67 | 55.08 | 43.92 | 9.34 | 1.33 | 0.52 |
| $CO_2$ | 3.60 | 0.67 | 3.60 | 3.60 | 3.60 | 0.77 | 0.09 | 0.53 |
| I | 59.40 | 11.11 | 59.40 | 59.40 | 59.40 | 12.63 | 1.81 | 0.50 |
| MEOH | 32.08 | 5.99 | 41.34 | 52.93 | 64.09 | 13.60 | 0.05 | 62.50 |
| TOTAL | 534.46 | 100.00 | 515.94 | 492.76 | 470.44 | 100.00 | 12.40 | 66.46 |

The temperature of the gas leaving bed 513 is 500° F., the temperature of the gas leaving bed 514 is 625° F., and the temperature of the gas leaving bed 515 is 730° F. The $C_1$, $C_2$ and $C_3$ catalysts are the same as those described in Example 1.

The stream in line 506 contains 6.0 percent methanol on a molar basis. At equilibrium the stream would have contained 13.6 mole percent methanol. The reaction to produce methanol approaches equilibrium to the extent of 47 percent, based upon the conversion of carbon monoxide, or 44 percent of methanol equilibrium.

The effluent from bed 515 flows through line 506 and through indirect heat-exchanger 516 wherein the effluent is cooled by means of indirect heat-exchanger with boiler feed water flowing through line 517. After having passed through heat-exchanger 516, the effluent is at a temperature of 400° F.

The effluent is then introduced into bed 518, initially contacting a bed of $C_1$ catalysts and then a bed 519 of $C_2$ catalyst, those catalysts having been defined in Example 1.

The effluent from bed 519 is at a temperature of 625° F. The effluent from bed 519 flows through line 508 and through indirect heat-exchanger 520 wherein the effluent is cooled by means of indirect heat-exchanger with boiler feed water, introduced through line 521. After having passed through heat-exchanger 520, the effluent is at a temperature of 400° F.

The effluent is then introduced into bed 522, there contacting a bed of $C_1$ catalyst, this catalyst having been defined in Example 1.

The effluent from bed 522 passes through line 509 and is at a temperature of 520° F. The stream in line 509 contains 13.6 percent methanol on a molar basis. At equilibrium, the stream would have contained 27.5 mole percent methanol. The reaction to produce methanol approaches equilibrium to the extent of 60 percent, based upon the conversion of carbon monoxide, or 50 percent of methanol equilibrium.

Stream 509 is cooled by passage through indirect heat-exchanger 523, by passage through indirect heat-exchanger 524 generating low pressure steam from boiler feed water introduced by means of line 527, and by passage through air cooler 525. The process stream leaving cooler 525 is introduced into separator 526 from the bottom of which liquid methanol, containing small quantities of dimethyl ether and higher alcohols, which is almost anhydrous, is removed through line 511.

A gaseous phase is removed overhead from separator 526 through line 528 and splits into streams 502 and 510. Stream 502 is returned into the synthesis loop, whereas stream 510 is purged.

For a 5,000 short ton per day methanol plant, there would be required approximately 5,500 cubic feet of catalyst. Because these catalysts will by design be functioning at different temperature and with different methanol partial pressures, as explained in Examples 1 and 3, the types and quantities will be distributed roughly as follows:

Bed 513, Catalyst $C_1$, volume approximately 400 ft$^3$
Bed 514, Catalyst $C_2$, volume approximately 600 ft$^3$
Bed 515, Catalyst $C_3$, volume approximately 1,000 ft$^3$
Bed 518, Catalyst $C_1$, volume approximately 900 ft$^3$
Bed 519, Catalyst $C_2$, volume approximately 1,100 ft$^3$
Bed 522, Catalyst $C_1$, volume approximately 1,500 ft$^3$ These are approximate volumes of catalyst and pertain to catalysts of the present art. However, as catalyst improvements are attained the quantities of catalyst in the reactors or trays and the type of distribution can be modified. The benefits to be attained by a more active catalyst are reduced pressure drop and reduced catalyst cost.

EXAMPLE 6

Figure 6:
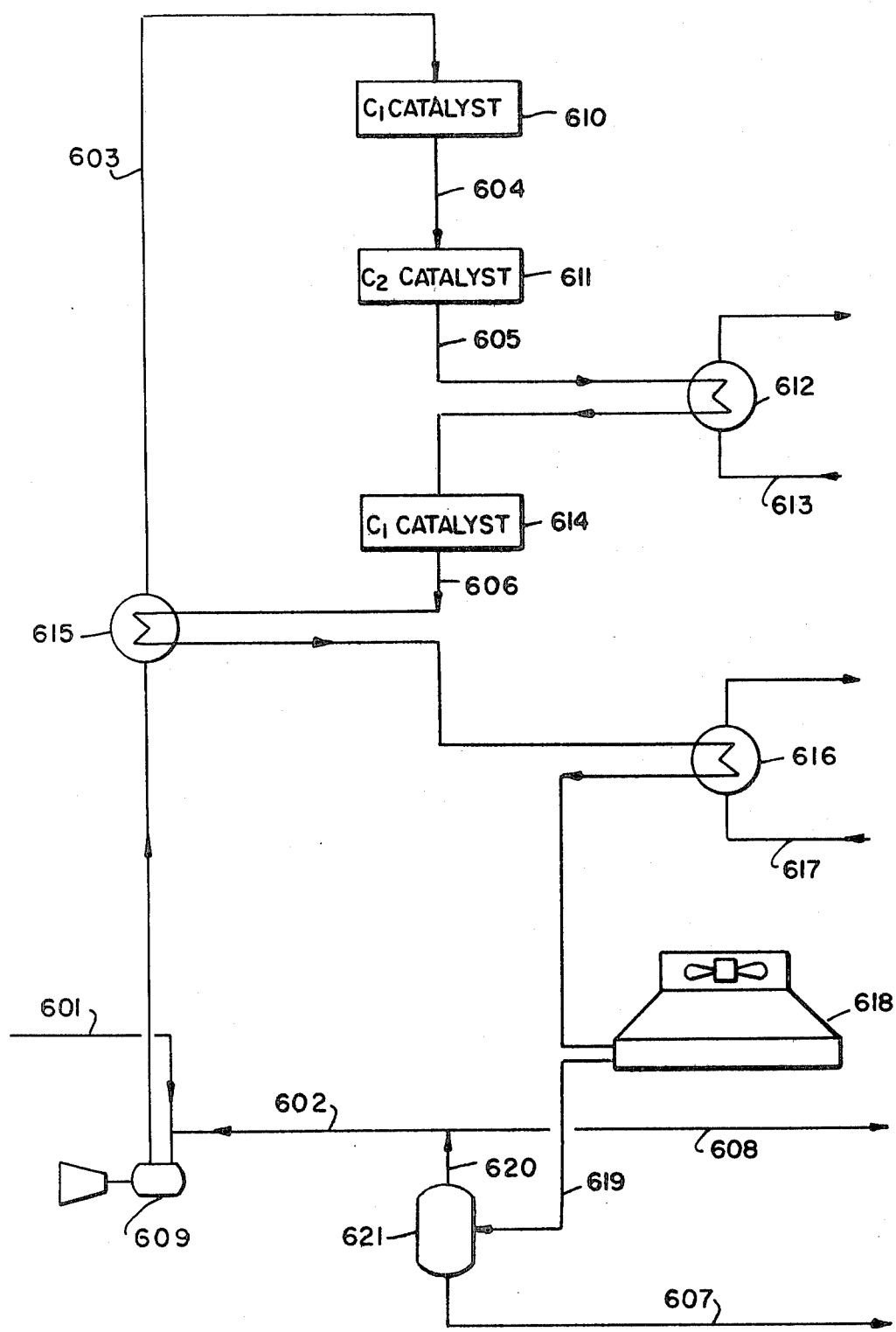

This Example describes an embodiment of this invention in which the synthesis gas is derived from coal and is to be considered in conjunction with FIG. 6 Table VI. FIG. 6 depicts a synthesis loop and Table VI gives the compositions of various streams shown in FIG. 6. In Table VI "I" signifies inerts and "M/T" signifies pound moles per short ton of methanol.

Referring to FIG. 6, fresh feed (make-up gas) is introduced into the synthesis loop at a pressure of 1,320 psi through line 601 and is admixed with recycle gas flowing through line 602. The mixed gas stream is then pumped by circulating compressor 609 through heat-exchanger 615, wherein the temperature of the gas is raised to 450° F. To produce one short ton of methanol, 101 brake horse power hours is supplied to compressor 609. Stream 603 passes through heat-exchanger 615, where it is heated to 450° F., as previously stated, and then for best results, can pass through a vessel (not shown in FIG. 6) containing a poison removal adsorbent as previously described herein.

TABLE VI

| STR | 601 | | 602 | | 603 | | 604 |
|---|---|---|---|---|---|---|---|
| COMP | M/T | % | M/T | % | M/T | % | M/T |
| $H_2$ | 139.61 | 67.08 | 930.22 | 71.51 | 1069.83 | 70.90 | 1026.27 |
| CO | 65.87 | 31.65 | 204.38 | 15.71 | 270.25 | 17.91 | 248.47 |
| $CO_2$ | 0.32 | 0.15 | 10.24 | 0.79 | 10.56 | 0.70 | 10.56 |
| I | 2.33 | 1.12 | 148.11 | 11.39 | 150.44 | 9.97 | 150.44 |
| MEOH | | | 7.85 | 0.60 | 7.85 | 0.52 | 29.63 |
| TOTAL | 208.13 | 100.00 | 1300.80 | 100.00 | 1508.93 | 100.00 | 1465.37 |

| STR | 605 | | 606 | | 607 | 608 |
|---|---|---|---|---|---|---|
| COMP | M/T | % | M/T | % | M/T | M/T |
| $H_2$ | 986.95 | 69.21 | 944.59 | 68.27 | 0.77 | 13.60 |
| CO | 228.81 | 16.04 | 207.63 | 15.01 | 0.26 | 2.99 |
| $CO_2$ | 10.56 | 0.74 | 10.56 | 0.76 | 0.17 | 0.15 |
| I | 150.44 | 10.55 | 150.44 | 10.87 | 0.17 | 2.16 |
| MEOH | 49.29 | 3.46 | 70.47 | 5.09 | 62.50 | 0.12 |
| TOTAL | 1426.05 | 100.00 | 1383.69 | 100.00 | 63.87 | 19.02 |

Stream 603, after purification, then passes through two beds of catalyst, C-1 and C-2, which are located in beds 610 and 611. The temperature of the gas leaving bed 610 is 540° F. and the temperature of the gas leaving bed 611 is 622° F., the temperature increasing because of the exothermal methanol reaction occurring in each catalyst bed. C-1 is a low temperature methanol synthesis catalyst which functions efficiently at pressures of 1,000 psi to 7,500 psi and at temperatures in the range of 400° F. This C-1 catalyst, as well as the C-2 and C-3 catalysts, have previously been described but will be described more fully in Examples 8, 9 and 10, hereinafter. After passing through beds 610 and 611, the temperature of the effluent of bed 611 is 622° F. The effluent contains 3.46/mol % methanol, which is a 49.4% approach to equilibrium, based on CO conversion.

The effluent from bed 611 flows through line 605 and then through indirect heat-exchanger 612, wherein the effluent is cooled by means of the indirect heat-exchange with boiler feed water introduced through line 613. After having passed through the heat-exchanger 612, the effluent gas is at a temperature of 450° F.

The gas is next introduced into bed 614 containing C-1 catalyst, from which it emerges at 540° F. The stream now in line 606 contains 5.09% methanol on a molar basis. At equilibrium the stream would contain 17.72% methanol. The reaction to produce methanol approaches equilibrium to the extent of 35.30%, based on the conversion of carbon monoxide.

Stream 606 is cooled by passage through indirect heat-exchanger 615, which preheats the gas for inlet to bed 610, and the gas in line 606 is thereby cooled to 228° F. The gas then passes through boiler feed water preheater 616, preheating the boiler feed water entering through line 617. The effluent gas is at 200° F. and passes into air cooler 618, which condenses the methanol and other products such as higher alcohols and dimethyl ether (in solution in the methanol). This gas-liquid mixture in line 619 passes into the separator 621. The liquid is removed from the separator through line 607, whereas the gas leaves via line 620. The gas leaving via 620 is divided into two streams, one passing through line 608 to purge and the balance passing through line 602 to the inlet to the recirculation pump to be recycled to the beds.

For a 5,000 short ton per day methanol plant there would be required approximately 7,500 cubic feet of catalyst. Because of the lower pressure than is stipulated in the earlier examples, the quantity of catalyst will be approximately 50% greater. This larger volume of catalyst will be distributed roughly as follows:

Bed 610, Catalyst $C_1$, volume approximately 2,000 ft$^3$
Bed 611, Catalyst $C_2$, volume approximately 2,500 ft$^3$
Bed 614, Catalyst $C_1$, volume approximately 3,000 ft$^3$

EXAMPLE 7

Figure 7:
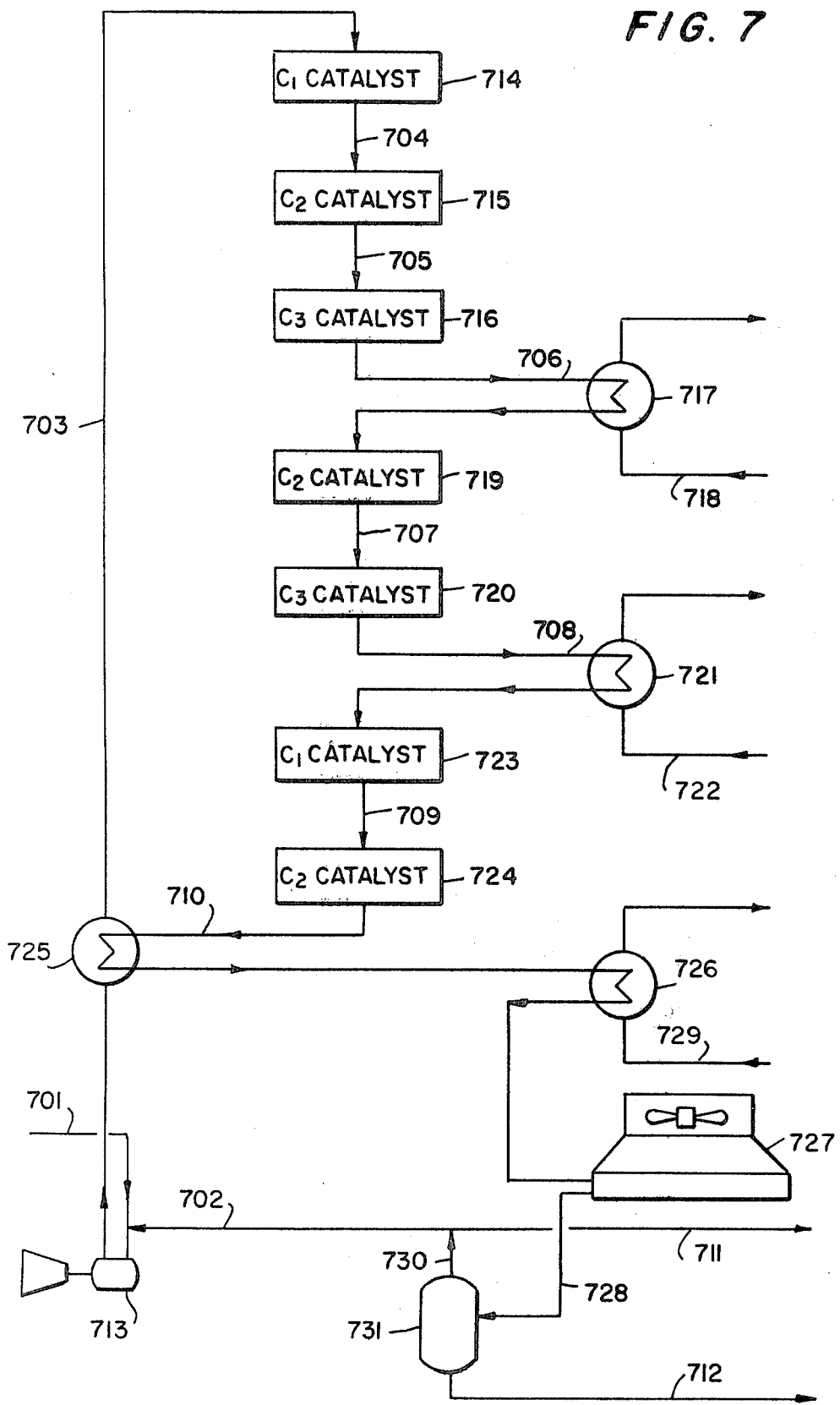

This Example describes an embodiment of this invention in which the synthesis gas is derived from coal and is to be considered in conjunction with FIG. 7 and Table VII. FIG. 7 depicts a synthesis loop and Table VII gives the compositions of various streams shown in FIG. 7. In Table VII "I" denotes inerts and "M/T" signifies pound moles per short ton of methanol.

Referring to FIG. 7, fresh feed (make-up gas) is introduced into the synthesis loop at a pressure of 6200 psi through line 701 and is admixed with recycle gas flowing through line 702. The mixed gas stream is then pumped by circulating compressor 713 through heat-exchanger 725, wherein the temperature of the gas is raised to 450° F.

Stream 703, after purification, passes through three beds of catalyst, C-b 1, C-2 and C-3, which are located in beds 714, 715 and 716, respectively. The temperature of the gas leaving bed 714 is 540° F., that leaving bed 715 is 630° F. and that leaving bed 716 is 730° F. The temperature increases because of the exothermal methanol synthesis reaction occurring in each catalyst bed. C-1 is the low temperature methanol catalyst which functions efficiently and without wax formation at pressures of 1000 to 7,500 psi and at temperatures in the range of 400° to 550° F. This C-1 catalyst, as well as the C-2 and C-3 catalysts, have been previously described herein, but will be described more fully in Examples 8, 9 and 10. After passing through the reactors 714, 715 and 716, the temperature of the effluent from reactor 716 is, as previously noted, 730° F. The gas contains 4.57/mol % methanol and is at 29.7% of approach to equilibrium, based on the CO conversion.

The effluent from reactor 716 flows through line 706 and through indirect heat-exchanger 717, wherein the effluent is cooled by indirect contact with boiler feed water introduced through line 718. After passing through the heat-exchanger 717, the effluent gas is at a temperature of 540° F.

The gas at 540° F. enters bed 719 charged with C-2 catalyst, from which it emerges at 630° F., and enters bed 720 charged with C-3 catalyst, from which it emerges at 730° F. The gas at this point contains 7.91/mol % methanol and is at a 48.5% approach to equilibrium, based on CO conversion.

The gas exits for bed 720 through line 708 and enters indirect heat-exchanger 721 where boiler feed water entering through line 722 is preheated, and the gas is thereby cooled to 450° F. as it emerges from the heat-exchanger.

The gas at 450° F. enters bed 723 charged with C-1 catalyst, from which it emerges at 540° F. and then enters bed 724 charged with C-2 catalyst, from which it emerges in line 710 and is at 615° F. The gas at this point contains 11.00/mol % methanol and is at 51.4% approach to equilibrium based on CO conversion.

Stream 710 is cooled by passage through indirect

TABLE VII

| STR | 701 | | 702 | | 703 | | 704 | 705 | 706 | |
|---|---|---|---|---|---|---|---|---|---|---|
| COMP | M/T | % | M/T | % | M/T | % | M/T | M/T | M/T | % |
| $H_2$ | 135.75 | 66.76 | 367.27 | 73.11 | 503.02 | 71.28 | 485.40 | 467.14 | 446.40 | 68.77 |
| CO | 64.63 | 31.78 | 62.40 | 12.42 | 127.03 | 18.00 | 118.22 | 109.09 | 98.72 | 15.21 |
| $CO_2$ | 0.70 | 0.34 | 3.25 | 0.65 | 3.95 | 0.56 | 3.95 | 3.95 | 3.95 | 0.61 |
| I | 2.28 | 1.12 | 68.08 | 13.55 | 70.36 | 9.97 | 70.36 | 70.36 | 70.36 | 10.84 |
| MEOH | | | 1.34 | 0.27 | 1.34 | 0.19 | 10.15 | 19.28 | 29.65 | 4.57 |
| TOTAL | 203.36 | 100.00 | 502.34 | 100.00 | 705.70 | 100.00 | 688.08 | 669.82 | 649.08 | 100.00 |

| STR | 707 | 708 | 709 | 710 | | 711 | 712 |
|---|---|---|---|---|---|---|---|
| COMP | M/T | M/T | M/T | M/T | % | M/T | M/T |
| $H_2$ | 428.98 | 408.96 | 392.34 | 377.96 | 65.09 | 6.95 | 3.74 |
| CO | 90.01 | 80.00 | 71.69 | 64.50 | 11.11 | 1.18 | 0.92 |
| $CO_2$ | 3.95 | 3.95 | 3.95 | 3.95 | 0.68 | 0.06 | 0.64 |
| I | 70.36 | 70.36 | 70.36 | 70.36 | 12.12 | 1.29 | 0.99 |
| MEOH | 38.36 | 48.37 | 56.68 | 63.87 | 11.00 | 0.03 | 62.50 |
| TOTAL | 631.66 | 611.64 | 595.02 | 580.64 | 100.00 | 9.51 | 68.79 |

To produce one short ton of methanol, 32 brake horse power hours is supplied to the compressor 713. Stream 703 passes through heat-exchanger 725 where, as previously stated, it is heated to 450° F., and then for best results can pass through a vessel (not shown in FIG. 7) containing a poison removal adsorbent as previously described herein.

heat-exchanger 725, which preheats the inlet gas in line 703, which is the feed to bed 714, the first in the sequence of beds. The cooled gas exiting from heat-exchanger 725 passes into indirect heat-exchanger 726 into which boiler feed water enters through line 729 and is preheated. The gas, on the other hand, is cooled to 200° F. and then for further cooling enters air cooler 727, from which it emerges in line 728 with the methanol at this point being condensed to the liquid phase together with any higher alcohols and other products including dimethyl ether which would be dissolved in the liquid phase.

The gas and liquid are separated in vessel 731 from which the crude methanol is removed through line 712. The gas phase is removed from the separator through line 730. The gas phase is separated into two streams, one passing through line 711 to be purged from the synthesis loop, whereas the other portion passes through line 702 to the compressor 713 for compression and entry into line 703 for recycle to the synthesis converter system.

For a 5,000 short ton per day methanol plant, there would be required approximately 5,000 cubic feet of catalysts. Because of the elevated pressure, there is a likelihood that a lesser quantity could be used, but because seven beds (or trays) are stipulated, it would be essential to have sufficient catalyst on each tray to ensure adequate residence time and avoidance of channeling. These factors would be important considerations in choosing catalyst volume, which could consequently be greater than that strictly required on a theoretical basis.

Bed 714, Catalyst $C_1$, volume approximately 300 ft$^3$
Bed 715, Catalyst $C_2$, volume approximately 400 ft$^3$
Bed 716, Catalyst $C_3$, volume approximately 800 ft$^3$
Bed 719, Catalyst $C_2$, volume approximately 600 ft$^3$
Bed 720, Catalyst $C_3$, volume approximately 800 ft$^3$
Bed 723, Catalyst $C_1$, volume approximately 900 ft$^3$
Bed 724, Catalyst $C_2$, volume approximately 1,200 ft$^3$

EXAMPLE 8

This Example describes the preparative procedure for one of the catalysts suitable for service as C-1, the low temperature catalyst of the invention. It also describes in less detail or enumerates other catalysts essentially as satisfactory and which may have special properties for special conditions of presence or absence of $CO_2$ in the gas stream and the desire for or against producing higher alcohols or dimethyl ether.

The preparative procedure for one of the most suitable C-1 catalysts is as follows:

1. Dissolve 1440 parts by weight of copper nitrate trihydrate and 297 parts by weight of zinc nitrate hexahydrate and 500 parts by weight of aluminum nitrate nonahydrate in 9,000 parts by weight of distilled water at 60° C. (140° F.) with vigorous agitation.

2. While maintaining the temperature at the 60° C. level, add ammonium carbonate as a solid over a period of one to two hours to the solution prepared in item 1 above until a pH of 6.6 to 6.8 has been reached.

3. Continue the agitation and maintain the temperature at 60° C. for an additional two hour digestion period.

4. After the digestion period filter the slurry and wash the filter cake on the filter with distilled water to remove ammonium nitrate, which would otherwise decompose and cause problems in ensuing operations. The copper, zinc, aluminum and ammonium salts should be free of iron, nickel and other foreign and harmful ions.

5. Dry the filter cake at 150° C. (302° F.).

6. Calcine the dry filter cake for 2 hours at 400° C. (752° F.).

7. Convert the dry filter cake to powder and then prepare pellets, preferably by first densifying, then mixing the densified powder with a pilling lubricant, and then finally pilling to one-fourth inch by one-fourth inch right cylinders.

8. Finally, heat treat the pills in air at 400° C. for two hours to increase porosity.

9. The pills so produced are then converted to useful methanol synthesis catalyst by reduction to reduced form of copper and zinc, using hydrogen as the reducing agent. The zinc reduces very little, whereas the copper is almost completely reduced. Reduction can be effected within the bed, or preferably externally, and then the catalyst can be introduced to form the bed as a stabilized catalyst. Reduction must be effected carefully with pure hydrogen diluted with an inert gas so as to avoid over-heating during reduction. Reduction can be effected at 200° to 300° C. (392° to 572° F.).

Instead of the 6 to one copper to zinc atomic ratio called for in item 1, above, one can use ratios from 8 to one copper atoms per atom of zinc.

Instead of the 11 weight % aluminum oxide stipulated also in item 1 above, one can use, instead, from two to as much as 99%, and instead of the aluminum being added as nitrate it can also be added as alumina hydrate in finely divided form.

Instead of the ammonium carbonate specified in item 2 above, one can use ammonia (anhydrous) with carbon dioxide, or ammonium bicarbonate. Sodium carbonate also can be used, but if one of the non-volatile carbonates is used, the powder after calcining must be slurried in a solution of ammonium bicarbonate at 0.1 to 1% weight concentration for an ion-exchange of the sodium with ammonium ion. The slurrying must be repeated until the sodium ion has been almost completely removed (less than 50 ppm in the finished catalyst).

Instead of the aluminum oxide, one can substitute other stabilizer-promoters, such as chromium (as trivalent or hexavalent with appropriate changes in preparative procedure), magnesium aluminum (spinel), cerium, rare earth mixtures, lanthanum, praseodymium, neodymium, zirconium, titanium, silicon, niobium and tantalum as the oxides or mixed oxides or solid state reaction products, used in varying ratios in the finished catalyst.

Instead of the nitrate salts of the copper, zinc and stabilizer (alumina), one can use the sulfate, chloride, acetate or other salts and, as in the case of the substitution of the sodium carbonate, it is necessary to slurry the calcined powder in ammonium bicarbonate solution to effect ion-exchange so that the foreign ion such as sulfate or chloride can be below the required 100 parts per million by weight in the finished catalyst. Even with the ion-exchange, the catalyst is noticeably less active than that prepared from the nitrate salts and ammonium carbonate precipitant.

EXAMPLE 9

This Example describes the preparative procedure for the catalyst designated as C-2 and is the one for the intermediate temperature range for methanol synthesis.

1. This item is exactly the same as for Example 8 with the exception that, instead of 1440 parts by weight of copper nitrate trihydrate, one uses 960 parts, and instead of 297 parts of zinc nitrate hexahydrate one uses 1188 parts. The aluminum nitrate nonahydrate parts by weight remain the same. This produces a one to one copper to zinc atomic ratio in the final catalyst, except for copper lost to ammine during the precipitation and subsequent filtration and washing. All other operations are the same as for Example 8.

All comments and alternatives pertaining to Example 8 also apply to this example, except that the copper to zinc atomic ratio should be maintained in the range of from 0.5 to 4 atoms of zinc per atom of copper. It is preferred that the amount of zinc be in the higher part of the range.

EXAMPLE 10

This Example describes the catalysts suitable for use in the high temperature bed, the catalyst designated C-3. This catalyst must be capable of withstanding high temperatures and must also be capable of effecting the reverse shift: $CO_2 + H_2 = CO + H_2O$. Consequently, there are conditions under which a mixed catalyst charge is preferred, and such will be described in this example. At least 5% of a catalyst especially effective for reverse shift reaction should be present in a mixed catalyst charge.

The single preferred catalyst, however, is made as follows:

1. Dissolve 482 parts by weight of copper nitrate trihydrate, 1188 parts by weight of zinc nitrate hexahydrate and 630 parts by weight of chromic acid anhydride ($CrO_3$) in 9000 parts by weight of distilled water. As above, all salts should be as free from iron and nickel contamination as possible. Adjust the temperature to 60° C. and agitate vigorously.

2. While maintaining the temperature at 60° to 70° C. and while agitating vigorously, add anhydrous ammonia to the solution of item 1 over a period of about one hour until a pH of 6.6 to 6.8 has been reached.

3. Continue agitation, but let the temperature drift lower for an additional two hours after the precipitation has been completed.

4. After the "digestion" period of item 3, the slurry is filtered and the filter cake is washed on the filter with distilled water to remove the ammonium nitrate which would otherwise decompose and cause problems in ensuing operations.

5. Dry the filter cake at 150° C.

6. Calcine the dry cake at 450° C. (842° F.) for 2 hours and then powder the dry cake.

7. Convert the powder of item 1 to pellets, preferably by first densifying, mixing with a pilling lubricant, and then pilling to right cylinders ¼inch by ¼inch.

8. Finally, heat treat the pills in air 500° C. (932° F.) for two hours to increase porosity.

9. The pills so produced can now be converted to a useful methanol synthesis catalyst with excellent reverse shift characteristics by reduction using dilute hydrogen to produce almost elemental copper and partially reduced zinc. The reduction must be conducted very carefully because of the presence of some chromium in hexavalent oxide form. Reduction can be effected at 250° to 350° C. Reduction can be effected in the bed, or preferably externally, and then stabilizing for transfer to the converter.

A satisfactory catalyst can be produced also using chromic acid and dissolving a stoichiometric or greater quantity of zinc therein. It is an inexpensive catalyst, but it is not effective for the reverse carbon monoxide shift. When this catalyst is used, it is preferable to mix equal portions of the first catalyst described in this example with it. It is also possible to mix some of the catalysts described for C-2 in it on a one to one volume basis.

As stated for example 8, salts other than nitrates can be used, but any offending ions must be eliminated in the finished catalyst by washing with ammonium bicarbonate solution so as to remove the alkali ions as well as the anions such as Cl and $SO_4$.

These catalysts in this example 10 can also be stabilized by the coprecipitation of the stabilizers given in example 8. These, under the higher temperature conditions pertaining for the environment for this catalyst C-3, can also act in some cases as promoters. Ceria and zirconia can, for example, beneficially affect the C-3 catalyst in its service. The weight ratio of stabilizer to catalyst can be in the range of 1 to 80 parts of stabilizer to 100 parts of catalyst.

Instead of the copper to zinc ratio of 1 to 2 stipulated in the item 1 of this example 9, the atom ratio can be 1 to 1 or as high as 1 to 6 (i.e., one Cu to six Zn) with appropriate changes in the chromic acid anhydride requirement.

Instead of the chromic acid anhydride, one can use a stoichiometric quantity of chromium nitrate. Furthermore, one can substitute the stabilizer promoters of Example 8 for the chromium (e.g., ceria, thoria, lanthana, zirconia, titania, mixed rare earth oxides, magnesia, silica, tantala, alumina, niobia, finely divided spinels, etc.). These can of course be added in varying ratios and can be intermixed and interreacted.

To prepare a catalyst for the third bed, the catalyst designated C-3, which is capable of producing higher alcohols, the catalyst is prepared containing a portion of manganese. The quantity of manganese can affect the quantities of higher alcohols produced, with the higher proportions of manganese producing higher quantities of higher alcohols. The manganese, copper, zinc and promoters and stabilizers are coprecipitated from the nitrates as described for example 8, the C-1 catalyst. Copper can be eliminated and so can the zinc, but a preferred atomic ratio is 1 Cu: 2 Zn: 0.5 Al, all as oxides. Instead of the Al, Ce, Zr and mixed rare earths, all as oxides, can be used. The catalyst is pelleted and heat treated as described in items 7 and 8.

Alkalis (sodium, potassium, rubidium and cesium) as carbonate, permanganate, chromate or silicate, for example, can also be added to a catalyst as promoters intended for enhanced higher alcohol production. The silica as silicate or as colloidal silica is also useful if it is desired to make increased quantities of dimethyl ether or similar oxygenated products. These can be added during the aforementioned densification operation.

EXAMPLE 11

This example describes the method of preparation of scavengers for trace poisons remaining in the synthesis gas even after the most careful removal methods of the present art. Because of the extremely large volumes of gases processed in methanol synthesis and which are passed over the synthesis catalysts, it is advisable that the level of poisons, such as sulfur, halide, carbonyls and vaporized solids, be reduced to the low parts per billion level.

The simplest and an extremely effective adsorbent for the poisons is the synthesis catalyst itself used in the first stage and designated C-1. When this catalyst has been used in the synthesis operation but is not functioning at an industrially economic level, it is removed and replaced with new catalyst. The used catalyst, although it is not functioning to an adequate level for methanol synthesis, will continue to function as an adsorbent for the aforementioned poisons. Consequently, the catalyst, when removed from the synthesis unit, can be simply recharged, after screening or abrasion and screening, to a guard vessel or upstream in the first stage reactor itself. The efficiency of the used catalyst for scavenging can be enhanced by pulverizing and repelleting in such a way as to introduce more porosity. This can be accomplished by incorporating a substance which can be vaporized or oxidized from the pellet. Substances such as ammonium carbonate, bicarbonate, oxalate, stearin, polyvinyl alcohol, cotton linters and the like are examples of the porosity-inducing agents. The procedure for pelleting can also be modified so as to produce low density and highly porous pellets. This is known in the art.

Other types of adsorbents, such as zinc oxides, manganese oxide, copper oxide, alone or mixed together with alkalis, such as sodium, potassium or other alkali metal oxides, or alkaline earth (calcium, strontium, and barium) carbonates, hydroxides or oxides are also effective when used as porous pellets or when supported in a highly dispersed manner on such supports as high surface alumina, silica, silica-alumina and other well known materials of this type. These can be fabricated in such a way as to induce high porosity, such as by the incorporation of "lost" volatiles or oxidizables or by utilizing a special low density pilling or pelleting operation. It is of course absolutely essential that the adsorbents do not contribute adversely to a reaction between $H_2$ and CO or $CO_2$ but this is almost axiomatic.

These scavengers can be operated at pressures pertaining in the methanol synthesis loop and of course at synthesis temperature or at temperatures below synthesis to as low as ambient.

The foregoing are presented as examples of the entire spectrum of scavengers rather than as a limitation on those which can be used. Many other combinations and extrapolations can be envisioned by one skilled in the art.

It will be apparent to one skilled in the art that instead of the catalysts being housed in separate converters, as described in the foregoing examples, these catalysts can be all housed in a single converter, with the catalysts separated into beds and the beds separated by solid plates in the converter. These plates would force the gas into exit lines passing into heat-exchangers and from the heat-exchangers back into a down-stream bed where reaction again takes place. The gas effluent from any given bed can again be forced from the converter, via a solid plate, into external heat-exchange (recovery) and back to additional bed (s) or, if desired, passed out of the converter for heat recovery and methanol condensation.

The following tabulation (Table VIII) summarizes the salient points in Examples 1 to 7 and has as its purpose a clarification and summary of the novelty of the invention.

TABLE VIII

| Example No. | Mode | Pressure Psi | Beds | Temperature Range | Energy Consumed Brake H.P. Hr. | Actual Concentration of MeOH in Exit Gas from Last Catalyst Bed |
|---|---|---|---|---|---|---|
| 1 | Invention | 4200 | 3 + 2 Interstage Cooling | 450° F.–750° F. | 52 | 7.48 Mol % |
| 2 | Art | 4200 | 5 No Cooling | 630° F.–720° F. | 89 | 4.18 Mol % |
| 3 | Invention | 3800 | 3 + 2 Interstage Cooling | 450° F.–720° F. | 50 | 7.5 Mol % |
| 4 | Art | 3800 | 5 No Cooling | 630° F.–720° F. | 90 | 4.05 Mol % |
| 5 | Invention | 4500 | 3 + 2 + 1 Interstage Cooling | 400° F.–730° F. | 27 | 13.6 Mol % |
| 6 | Invention | 1320 | 2 + 1 Interstage Cooling | 450° F.–622° F. | 101 | 5.09 Mol % |
| 7 | Invention | 6200 | 3 + 2 + 2 Interstage Cooling | 450° F.–730° F. | 32 | 11.00 Mol % |

The tabulation above demonstrates the superiority of the invention in respect to power consumption per unit of methanol and percentage of methanol in the product gas (making condensation of product more efficient and minimizing recirculation costs for the synthesis gas).

What is claimed is:

1. In the process for the synthesis of methanol wherein a gaseous mixture containing hydrogen and carbon monoxide, carbon dioxide or a mixture of carbon monoxide and carbon dioxide is passed under elevated conditions of temperature and pressure into contact with a catalyst wherein the improvement comprises the steps of
   (a) passing said mixture through two or more beds of catalyst arranged in series, the catalyst in each of said beds being of such composition as to function in a lower temperature range than the catalyst in each succeeding bed, said mixture being introduced into the first bed at a temperature within the range from 400° F. to 500° F. and exiting the last bed at a temperature within the range from 700° F. to 750° F.,
   (b) cooling the mixture to a temperature within the range from 400° F. to 500° F. by indirect heat-exchange, and
   (c) passing the mixture through one or more beds of catalyst whereby the temperature of mixture is raised to from 550° F. to 650° F.

2. The process of claim 1 wherein the pressure is within the range from 1000 psi to 7500 psi.

3. The process of claim 1 wherein the mixture of carbon monoxide and carbon dioxide is composed of at least two-thirds carbon monoxide by volume, based upon the total volume of carbon monoxide and carbon dioxide.

4. The process of claim 1 wherein in step (a) three beds of catalyst are arranged in series, the bed initially contacted by the gaseous mixture being composed of catalyst which functions over temperatures within the range from 400° F. to 550° F. to produce methanol from hydrogen and carbon monoxide, the next bed contacted by the gaseous mixture being composed of catalyst which functions over temperatures within the range from 500° F. to 630° F. to produce methanol from hydrogen and carbon monoxide, the third bed contacted by the gaseous mixture being composed of catalyst which functions over temperatures within the range from 600° F. to 750° F. to produce methanol from hydrogen and carbon monoxide, and wherein in step (c) two beds of catalyst are arranged in series, the bed initially contacted by the gaseous mixture in step (c) being composed of catalyst which functions over temperatures within the range from 400° F. to 550° F. to produce methanol from hydrogen and carbon monoxide, and the second bed contacted by the gaseous mixture being composed of catalyst which functions over temperatures within the range from 500° F. to 650° F. to produce methanol from hydrogen and carbon monoxide.

5. In the process for the synthesis of methanol wherein a gaseous mixture containing hydrogen and carbon monoxide, carbon dioxide or a mixture of carbon monoxide and carbon dioxide is passed under elevated conditions of temperature and pressure into contact with a catalyst wherein the improvement comprises the steps of (a) passing said mixture through three beds of catalyst arranged in series, the catalyst in each of said beds being of such composition as to function at a lower temperature range than the catalyst in each succeeding bed, said mixture being introduced into the first bed at a temperature within the range from 400° F. to 500° F. and exiting the third bed at a temperature within the range from 700° F. to 750° F., (b) cooling the mixture to a temperature within the range from 400° F. to 500° F. by indirect heat-exchange, (c) passing the mixture through two further beds of catalyst arranged in series, the catalyst in the first of such beds being of such composition as to function at a lower temperature range than the catalyst in the second of such beds, the mixture being introduced into the first of such beds at a temperature within the range from 400° F. to 500° F. and exiting the second of such beds at a temperature within the range from 500° F. to 650° F., (d) cooling the mixture to a temperature within the range from 400° F. to 500° F. by indirect heat-exchange, and (e) passing the mixture through one further bed of catalyst, the mixture being introduced into such bed at a temperature within the range from 400° F. to 500° F. and exiting such bed at a temperature within the range from 500° F. to 550° F.

6. The process of claim 5 wherein in steps (a) and (c) the bed of catalyst initially contacted by the mixture is composed of catalyst which functions over temperatures within the range from 400° F. to 550° F. to produce methanol from hydrogen and carbon monoxide, wherein in steps (a) and (c) the next bed of catalyst contacted by the mixture is composed of catalyst which functions over temperatures within the range from 500° F. to 630° F. to produce methanol from hydrogen and carbon monoxide, and wherein in step (a) the third bed of catalyst contacted by the mixture is composed of catalyst which functions over temperatures within the range from 600° F. to 750° F. to produce methanol from hydrogen and carbon monoxide.

7. The process of claim 1 wherein each catalyst contains copper and zinc.

8. The process of claim 4 wherein in steps (a) and (c) the bed initially contacted by the gaseous mixture is composed of catalyst which contains from one to 6 atoms of copper per atom of zinc.

9. The process of claim 5 wherein in steps (a), (c) and (e) the bed initially contacted by the gaseous mixture is composed of catalyst which contains from one to 6 atoms of copper per atom of zinc.

10. The process of claim 4 wherein in steps (a) and (c) the second bed contacted by the gaseous mixture is composed of catalyst which contains from 0.5 to 4 atoms of zinc per atom of copper.

11. The process of claim 5 wherein in step (a) the third bed contacted by the gaseous mixture is composed of catalyst which contains from one to six atoms of zinc per atom of copper.

12. The process of claim 1 wherein the catalyst contains a stabilizing amount of an oxide of aluminum, chromium, magnesium, cerium, rare earth mixtures, lanthanum, praseodymium, neodymium, zirconium, titanium, silicon, niobium or tantalum or a mixture thereof.

13. The process of claim 5 wherein in step (e) the catalyst contains manganese as oxide in amount sufficient to promote the production of higher alcohols.

14. The process of claim 4 wherein in steps (a) and (c) the first two beds contacted by the gaseous mixture are composed of catalyst which contains copper and zinc and wherein in step (a) the third bed contacted by the gaseous mixture is composed of catalyst which contains zinc.

* * * * *

UNITED STATES PATENT AND TRADEMARK OFFICE
CERTIFICATE OF CORRECTION

PATENT NO. : 4,235,799     Page 1 of 2
DATED : Nov. 25, 1980
INVENTOR(S) : Wentworth et al.

It is certified that error appears in the above—identified patent and that said Letters Patent is hereby corrected as shown below:

Col. 5, line 18, change "satls" to -- salts --

Col. 6, line 47, change "$C_1$" to -- $C_2$ --

Line 56, change "mopst" to -- most --

Col. 7, line 10, change "physicl" to -- physical --

Line 38, change "cn" to -- can --

Line 44, change "physicl" to -- physical --

Col. 13, line 7, change "Chd 3" to -- $C_3$ --

Line 60, change "$C^3$" to -- $C_3$ --

Col. 14, line 12, change "heat-exchanger" to -- heat-exchange --

Col. 16, line 21, change "Chd 2" to -- $C_2$ --

Col. 20 line 2, change "C-b 1" to -- C-1 --

UNITED STATES PATENT AND TRADEMARK OFFICE
CERTIFICATE OF CORRECTION

PATENT NO. : 4,235,799

DATED : Nov. 25, 1980

INVENTOR(S) : Wentworth et al.

It is certified that error appears in the above-identified patent and that said Letters Patent are hereby corrected as shown below:

In FIG. 2, the vertical line between elements 220 and 221 should be identified as -- 209 --; and the vertical line between elements 221 and 222 should be identified as -- 211 --

In FIG. 4, the horizontal line intersecting line 411 should be identified as -- 412 --

Signed and Sealed this

Tenth Day of March 1981

[SEAL]

Attest:

RENE D. TEGTMEYER

Attesting Officer

Acting Commissioner of Patents and Trademarks